(12) United States Patent
Severns

(10) Patent No.: US 10,945,892 B2
(45) Date of Patent: Mar. 16, 2021

(54) INCONTINENCE DETECTION SYSTEM AND DETECTORS

(71) Applicant: Hill-Rom Services, Inc., Batesville, IN (US)

(72) Inventor: Ryan Severns, Grand Rapids, MI (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 16/407,258

(22) Filed: May 9, 2019

(65) Prior Publication Data

US 2019/0365573 A1 Dec. 5, 2019

Related U.S. Application Data

(60) Provisional application No. 62/678,676, filed on May 31, 2018, provisional application No. 62/687,926, filed on Jun. 21, 2018.

(51) Int. Cl.
| | |
|---|---|
| *A61F 13/42* | (2006.01) |
| *A61F 5/48* | (2006.01) |
| *G06K 7/10* | (2006.01) |
| *G01N 27/04* | (2006.01) |
| *G08B 21/20* | (2006.01) |
| *A61F 13/84* | (2006.01) |

(52) U.S. Cl.
CPC .............. *A61F 13/42* (2013.01); *A61F 5/485* (2013.01); *G01N 27/048* (2013.01); *G06K 7/10366* (2013.01); *G08B 21/20* (2013.01); *A61F 2013/424* (2013.01); *A61F 2013/8482* (2013.01)

(58) Field of Classification Search
CPC .... A61F 13/42; A61F 5/485; A61F 2013/424; A61F 2013/8482; G01N 27/048; G06K 7/10366; G08B 21/20
USPC ........................................................ 340/573.5
See application file for complete search history.

(56) References Cited

U.S. PATENT DOCUMENTS

| | | |
|---|---|---|
| 1,772,232 A | 8/1930 | Guilder |
| 2,127,538 A | 8/1938 | Seiger |
| 2,644,050 A | 6/1953 | Seiger |
| 2,668,202 A | 2/1954 | Kaplan |
| 2,726,294 A | 12/1955 | Kroening et al. |
| 2,907,841 A | 10/1959 | Campbell |
| 3,199,095 A | 8/1965 | Ashida |
| 3,971,371 A | 7/1976 | Bloom |
| 4,069,817 A | 1/1978 | Fenote et al. |
| 4,106,001 A | 8/1978 | Mahoney |
| 4,163,449 A | 8/1979 | Regal |
| 4,191,950 A | 3/1980 | Levin et al. |
| 4,212,295 A | 7/1980 | Snyder |
| 4,228,426 A | 10/1980 | Roberts |

(Continued)

FOREIGN PATENT DOCUMENTS

| | | |
|---|---|---|
| CN | 206334019 U | 7/2017 |
| WO | 2017087452 A1 | 5/2017 |

*Primary Examiner* — Omar Casillashernandez
(74) *Attorney, Agent, or Firm* — Barnes & Thornburg LLP

(57) ABSTRACT

An incontinence detector includes a layer of material having uniformly distributed electrically resistive elements which impart a baseline electrical resistance to the layer. The layer also has an actual electrical resistance. The detector also includes an RFID tag having a first and second leads which extend into the material without contacting each other. The tag is responsive to deviations of the actual resistance from the baseline resistance.

14 Claims, 18 Drawing Sheets

(56) References Cited

U.S. PATENT DOCUMENTS

| | | |
|---|---|---|
| 4,347,503 A | 8/1982 | Uyehara |
| 4,539,559 A | 9/1985 | Kelley et al. |
| 4,747,166 A | 5/1988 | Kuntz |
| 4,965,554 A | 10/1990 | Darling |
| 5,081,422 A | 1/1992 | Shih |
| 5,086,294 A | 2/1992 | Schwab, Jr. |
| 5,137,033 A | 8/1992 | Norton |
| 5,144,284 A | 9/1992 | Hammett |
| 5,291,181 A | 3/1994 | De Ponte |
| 5,438,721 A | 8/1995 | Pahno et al. |
| 5,459,452 A | 10/1995 | DePonte |
| 5,491,609 A | 2/1996 | Dankman et al. |
| 5,537,095 A | 7/1996 | Dick et al. |
| 5,675,854 A | 10/1997 | Zibelin |
| 5,760,694 A | 6/1998 | Nissim |
| 5,790,035 A | 8/1998 | Ho |
| 5,824,883 A | 10/1998 | Park et al. |
| 5,910,080 A | 6/1999 | Selton |
| 5,947,943 A | 9/1999 | Lee |
| 6,028,241 A | 2/2000 | Armstead |
| 6,047,419 A | 4/2000 | Fergusaon |
| 6,104,311 A | 8/2000 | Lastinger |
| 6,292,102 B1 | 9/2001 | Smith |
| 6,340,932 B1 | 1/2002 | Rodgers et al. |
| 6,341,393 B1 | 1/2002 | Votel |
| 6,351,215 B2 | 2/2002 | Rodgers et al. |
| 6,362,737 B1 | 3/2002 | Rodgers et al. |
| 6,384,728 B1 | 5/2002 | Kanor et al. |
| 6,544,200 B1 | 4/2003 | Smith et al. |
| 6,552,661 B1 | 4/2003 | Lastinger et al. |
| 6,583,722 B2 | 6/2003 | Jeutter et al. |
| 6,603,403 B2 | 8/2003 | Jeutter et al. |
| 6,621,410 B1 | 9/2003 | Lastinger et al. |
| 6,639,517 B1 | 10/2003 | Chapman et al. |
| 6,774,800 B2 | 8/2004 | Friedman et al. |
| 6,831,562 B2 | 12/2004 | Rodgers et al. |
| 6,832,507 B1 | 12/2004 | van de Berg et al. |
| 6,876,303 B2 | 4/2005 | Reeder et al. |
| 6,933,849 B2 | 8/2005 | Sawyer |
| 6,948,205 B2 | 9/2005 | Van Der Wurf et al. |
| 6,982,646 B2 | 1/2006 | Rodgers et al. |
| 7,017,213 B2 | 3/2006 | Chisari |
| 7,030,731 B2 | 4/2006 | Lastinger et al. |
| 7,071,830 B2 | 7/2006 | Sahlberg et al. |
| 7,120,952 B1 | 10/2006 | Bass et al. |
| 7,181,206 B2 | 2/2007 | Pedersen |
| 7,250,547 B1 | 7/2007 | Hofmeister et al. |
| 7,253,729 B2 | 8/2007 | Lastinger et al. |
| 7,274,944 B2 | 9/2007 | Lastinger et al. |
| 7,302,278 B2 | 11/2007 | Lastinger et al. |
| 7,305,246 B2 | 12/2007 | Lastinger et al. |
| 7,308,270 B2 | 12/2007 | Lastinger et al. |
| 7,348,930 B2 | 3/2008 | Lastinger et al. |
| 7,349,701 B2 | 3/2008 | Lastinger et al. |
| 7,355,090 B2 | 4/2008 | Ales, III et al. |
| 7,359,675 B2 | 4/2008 | Lastinger et al. |
| 7,394,391 B2 | 7/2008 | Long |
| 7,400,860 B2 | 7/2008 | Lastinger et al. |
| 7,424,298 B2 | 9/2008 | Lastinger et al. |
| 7,429,689 B2 | 9/2008 | Chen et al. |
| 7,489,252 B2 | 2/2009 | Long et al. |
| 7,489,282 B2 | 2/2009 | Lastinger et al. |
| 7,498,478 B2 | 3/2009 | Long et al. |
| 7,551,089 B2 | 6/2009 | Sawyer |
| 7,586,385 B2 | 9/2009 | Rokhsaz |
| 7,595,734 B2 | 9/2009 | Long et al. |
| 7,595,756 B2 | 9/2009 | Lastinger et al. |
| 7,598,853 B2 | 10/2009 | Becker et al. |
| 7,598,862 B2 | 10/2009 | Lastinger et al. |
| 7,599,699 B2 | 10/2009 | Lastinger et al. |
| 7,616,959 B2 | 11/2009 | Spenik et al. |
| 7,633,378 B2 | 12/2009 | Rodgers et al. |
| 7,649,125 B2 | 1/2010 | Ales, III et al. |
| 7,663,483 B2 | 2/2010 | Spenik et al. |
| 7,667,600 B2 | 2/2010 | Woodbury et al. |
| 7,812,731 B2 | 10/2010 | Bunza et al. |
| 7,822,386 B2 | 10/2010 | Lastinger et al. |
| 7,834,234 B2 | 11/2010 | Roe et al. |
| 7,834,235 B2 | 11/2010 | Long et al. |
| 7,834,765 B2 | 11/2010 | Sawyer |
| 7,834,766 B2 | 11/2010 | Sawyer |
| 7,838,720 B2 | 11/2010 | Roe et al. |
| 7,849,544 B2 | 12/2010 | Flocard et al. |
| 7,873,319 B2 | 1/2011 | Lastinger et al. |
| 7,977,529 B2 | 7/2011 | Bergman et al. |
| 8,009,646 B2 | 8/2011 | Lastinger et al. |
| 8,073,386 B2 | 12/2011 | Pedersen |
| 8,081,043 B2 | 12/2011 | Rokhsaz |
| 8,102,254 B2 | 1/2012 | Becker et al. |
| 8,104,126 B2 | 1/2012 | Caminade et al. |
| 8,106,782 B2 | 1/2012 | Fredriksson et al. |
| 8,111,165 B2 | 2/2012 | Ortega et al. |
| 8,111,678 B2 | 2/2012 | Lastinger et al. |
| 8,121,856 B2 | 2/2012 | Huster et al. |
| 8,181,290 B2 | 5/2012 | Brykalski et al. |
| 8,191,187 B2 | 6/2012 | Brykalski et al. |
| 8,196,809 B2 | 6/2012 | Thorstensson |
| 8,237,572 B2 | 8/2012 | Clement et al. |
| 8,248,249 B2 | 8/2012 | Clement et al. |
| 8,270,383 B2 | 8/2012 | Lastinger et al. |
| 8,279,069 B2 | 10/2012 | Sawyer |
| 8,319,633 B2 | 11/2012 | Becker et al. |
| 8,325,695 B2 | 12/2012 | Lastinger et al. |
| 8,332,975 B2 | 12/2012 | Brykalski et al. |
| 8,334,226 B2 | 12/2012 | Nhan et al. |
| 8,345,651 B2 | 1/2013 | Lastinger et al. |
| 8,372,766 B2 | 2/2013 | Nhan et al. |
| 8,395,014 B2 | 3/2013 | Helmer et al. |
| 8,428,039 B2 | 4/2013 | Lastinger et al. |
| 8,428,605 B2 | 4/2013 | Pedersen et al. |
| 8,461,982 B2 | 6/2013 | Becker et al. |
| 8,482,305 B2 | 7/2013 | Johnson |
| 8,487,774 B2 | 7/2013 | Reeder et al. |
| 8,502,684 B2 | 8/2013 | Bunza et al. |
| 8,628,506 B2 | 1/2014 | Ales, III et al. |
| 8,674,826 B2 | 3/2014 | Becker et al. |
| 8,697,934 B2 | 4/2014 | Nhan et al. |
| 8,742,929 B2 | 6/2014 | Sawyer |
| 8,749,319 B2 | 6/2014 | Rokhsaz et al. |
| 8,766,804 B2 | 7/2014 | Reeder et al. |
| 8,842,013 B2 | 9/2014 | Sawyer |
| 8,855,089 B2 | 10/2014 | Lastinger et al. |
| 8,866,615 B2 | 10/2014 | Sawyer |
| 8,878,557 B2 | 11/2014 | Kristiansen et al. |
| 8,878,676 B2 | 11/2014 | Koblasz |
| 8,896,449 B2 | 11/2014 | Sawyer |
| 8,914,923 B2 | 12/2014 | Smith |
| 8,933,292 B2 | 1/2015 | Abraham et al. |
| 8,962,909 B2 | 2/2015 | Groosman et al. |
| 8,978,452 B2 | 3/2015 | Johnson et al. |
| 9,048,819 B2 | 6/2015 | Rokhsaz et al. |
| 9,107,776 B2 | 8/2015 | Bergman et al. |
| 9,160,054 B2 | 10/2015 | Yu et al. |
| 9,323,797 B2 | 4/2016 | Acree |
| 9,366,644 B1 | 6/2016 | Lastinger et al. |
| 9,506,886 B1 | 11/2016 | Woodbury et al. |
| 9,649,230 B1 | 5/2017 | Li |
| 9,675,502 B2 | 6/2017 | Goda et al. |
| 9,719,951 B1 | 8/2017 | Woodbury et al. |
| 10,022,277 B2 | 7/2018 | Heil et al. |
| 10,159,607 B2 | 12/2018 | Monson et al. |
| 10,500,105 B2 | 12/2019 | Monson et al. |
| 10,682,263 B2 * | 6/2020 | Heil ............... A61B 5/6892 |
| 2002/0011932 A1 | 1/2002 | Rodgers et al. |
| 2002/0033757 A1 | 3/2002 | Rodgers et al. |
| 2002/0145525 A1 | 10/2002 | Friedman et al. |
| 2002/0145526 A1 | 10/2002 | Friedman et al. |
| 2003/0030568 A1 | 2/2003 | Lastinger et al. |
| 2005/0003763 A1 | 1/2005 | Lastinger et al. |
| 2005/0003865 A1 | 1/2005 | Lastinger et al. |
| 2005/0046578 A1 | 3/2005 | Pires |
| 2005/0052282 A1 | 3/2005 | Rodgers et al. |
| 2005/0060246 A1 | 3/2005 | Lastinger et al. |
| 2005/0174246 A1 | 8/2005 | Picco et al. |

(56) References Cited

U.S. PATENT DOCUMENTS

| | | |
|---|---|---|
| 2005/0242946 A1 | 11/2005 | Hubbard, Jr. et al. |
| 2005/0250453 A1 | 11/2005 | Lastinger et al. |
| 2005/0277441 A1 | 12/2005 | Lastinger et al. |
| 2005/0282545 A1 | 12/2005 | Lastinger et al. |
| 2005/0282553 A1 | 12/2005 | Lastinger et al. |
| 2006/0164320 A1 | 7/2006 | Lastinger et al. |
| 2006/0270351 A1 | 11/2006 | Lastinger et al. |
| 2007/0159332 A1 | 7/2007 | Koblasz |
| 2007/0202809 A1 | 8/2007 | Lastinger et al. |
| 2007/0270774 A1 | 11/2007 | Bergman et al. |
| 2008/0116990 A1 | 5/2008 | Rokhsaz |
| 2008/0204245 A1 | 8/2008 | Blair et al. |
| 2008/0262376 A1 | 10/2008 | Price |
| 2008/0263776 A1 | 10/2008 | O'Reagan et al. |
| 2008/0300559 A1 | 12/2008 | Gustafson et al. |
| 2009/0160648 A1 | 6/2009 | Rokhsaz |
| 2009/0289743 A1 | 11/2009 | Rokhsaz |
| 2009/0292265 A1 | 11/2009 | Helmer et al. |
| 2009/0315728 A1 | 12/2009 | Ales, III et al. |
| 2009/0326417 A1 | 12/2009 | Ales, III et al. |
| 2010/0043143 A1 | 2/2010 | O'Reagan et al. |
| 2011/0025458 A1 | 2/2011 | Rokhsaz et al. |
| 2011/0025473 A1 | 2/2011 | Rokhsaz et al. |
| 2011/0092890 A1 | 4/2011 | Stryker et al. |
| 2011/0115635 A1 | 5/2011 | Petrovski et al. |
| 2011/0263952 A1 | 10/2011 | Bergman et al. |
| 2011/0283459 A1 | 11/2011 | Essers |
| 2011/0291810 A1 | 12/2011 | Rokhsaz et al. |
| 2011/0295619 A1 | 12/2011 | Tough |
| 2011/0300808 A1 | 12/2011 | Rokhsaz et al. |
| 2011/0302720 A1 | 12/2011 | Yakam et al. |
| 2011/0309937 A1 | 12/2011 | Bunza et al. |
| 2012/0092027 A1 | 4/2012 | Forster |
| 2012/0105233 A1 | 5/2012 | Bobey et al. |
| 2012/0119912 A1 | 5/2012 | Ortega et al. |
| 2012/0130330 A1 | 5/2012 | Wilson et al. |
| 2012/0165772 A1 | 6/2012 | Groosman et al. |
| 2012/0216607 A1 | 8/2012 | Sjöholm et al. |
| 2012/0217311 A1 | 8/2012 | Rokhsaz et al. |
| 2012/0268278 A1 | 10/2012 | Lewis et al. |
| 2013/0019405 A1 | 1/2013 | Flanagan et al. |
| 2013/0079590 A1 | 3/2013 | Bengtson |
| 2013/0109929 A1 | 5/2013 | Menzel |
| 2013/0123726 A1 | 5/2013 | Yu et al. |
| 2013/0254141 A1 | 9/2013 | Barda et al. |
| 2013/0324955 A1* | 12/2013 | Wong .................. A61F 13/42 604/361 |
| 2014/0120836 A1 | 5/2014 | Rokhsaz et al. |
| 2014/0148772 A1 | 5/2014 | Hu et al. |
| 2014/0152442 A1 | 6/2014 | Li |
| 2014/0200538 A1* | 7/2014 | Euliano .............. G01N 27/121 604/361 |
| 2014/0236629 A1 | 8/2014 | Kim et al. |
| 2014/0244644 A1 | 8/2014 | Mashinchi et al. |
| 2014/0247125 A1 | 9/2014 | Barsky |
| 2014/0266735 A1 | 9/2014 | Riggio et al. |
| 2014/0276504 A1 | 9/2014 | Heil et al. |
| 2014/0296808 A1 | 10/2014 | Curran et al. |
| 2014/0358099 A1 | 12/2014 | Durgin et al. |
| 2015/0080819 A1 | 3/2015 | Charna et al. |
| 2015/0080834 A1 | 3/2015 | Mills |
| 2015/0087935 A1 | 3/2015 | Davis et al. |
| 2016/0267769 A1 | 9/2016 | Rokhsaz et al. |
| 2017/0098044 A1* | 4/2017 | Lai ...................... G06F 19/00 |
| 2017/0135884 A1 | 5/2017 | Lachenbruch et al. |
| 2017/0246063 A1 | 8/2017 | Monson et al. |
| 2018/0021184 A1 | 1/2018 | Monson et al. |
| 2018/0036180 A1* | 2/2018 | Long .................. G06K 9/00771 |
| 2019/0060137 A1 | 2/2019 | Severns et al. |
| 2019/0091074 A1 | 3/2019 | Monson et al. |
| 2019/0220636 A1* | 7/2019 | Yeh .................... G06F 12/0802 |

* cited by examiner

INCONTINENCE DETECTION SYSTEM AND DETECTORS

CROSS-REFERENCE TO RELATED PATENT APPLICATIONS

This application claims priority to U.S. Provisional Applications 62/678,676 entitled "Incontinence Detection System and Detectors" filed on May 31, 2018 and 62/687,926 entitled "Incontinence Detection System and Detectors" filed on Jun. 21, 2018, the contents of both of which are incorporated herein by reference.

TECHNICAL FIELD

The subject matter described herein relates to a system and detectors for detecting incontinence events, in particular to a device that employs a layer of material having uniformly distributed electrically resistive elements and a device that relates electrical resistance to depth of penetration of liquid arising from an incontinence event.

BACKGROUND

Incontinence detection devices are used in health care facilities and in residential settings to detect if an occupant of a bed has suffered an incontinence event (accidental discharge of urine and/or liquid or loose fecal matter).

One example of an incontinence detection device is a thin pad having a pair of electrical traces (i.e. electrodes) arranged in an open circuit configuration. The pad includes an RFID tag which has a pair of terminals and a pair of associated tamper inputs. Each trace is connected to one of the terminals. The pad is placed between the bed occupant and the sleep surface (mattress).

When the pad is dry the electrical resistance between the tamper inputs is high (e.g. 20 MΩ). The presence of an electrically conductive liquid, such as urine, in sufficient quantity to bridge between the two traces, reduces the electrical resistance between the tamper inputs. The reduced resistance reveals the presence of the liquid.

Despite the merits of the incontinence detection device described above, liquid detection depends on the in-plane spacing of the traces. A spacing which is too large may cause false negative results (failure to detect an incontinence event). A spacing which is too small may cause false positives (e.g. interpreting normally occurring amounts of perspiration or a minor spill of drinking water as an incontinence event). Because the spacing of the traces differs at different parts of the pad, the detection accuracy of the pad may be better in some places than in others. In addition, the pad is not well suited to detecting depth of liquid penetration.

What is needed is an incontinence detection device that addresses the foregoing challenges.

SUMMARY

The present invention may comprise one or more of the features recited in the appended claims and/or one or more of the following features or combinations thereof.

One embodiment of an incontinence detector described herein includes a layer of material having uniformly distributed electrically resistive elements. The electrically resistive elements impart a baseline electrical resistance to the layer. The layer also has an actual electrical resistance. The detector includes an RFID tag. First and second leads extend from the RFID tag into the layer of material without contacting each other. The tag is responsive to deviations of the actual resistance from the baseline resistance.

Another embodiment of an incontinence detection system includes a pad with carbon fiber segments uniformly distributed through the pad. The pad has a dry electrical resistance when the pad is dry and a wet electrical resistance when the pad is wet with an electrically conductive liquid. The wet electrical resistance is less than the dry electrical resistance. The system also includes a processor and machine readable instructions. When the instructions are executed by the processor the system responds in a first way to the dry electrical resistance and responds in a second way to the wet electrical resistance.

Another embodiment of the incontinence detector includes a first layer of material having a first baseline electrical resistance and a first actual electrical resistance, and a second layer of material having a second baseline electrical resistance and a second actual electrical resistance. The incontinence detector also includes a processor which operates according to machine readable instructions so that the detector responds by relating the actual resistances to a liquid related occurrence.

Another embodiment of an incontinence detector includes first through Nth layers of material (where N≥2). Each layer has a baseline electrical resistance and an actual electrical resistance. The detector also has first through Mth intermediate layers alternating with the N material layers such that each intermediate layer separates two of the N layers of material from each other. The detector also includes a processor which operates according to machine readable instructions so that the detector responds by relating the actual resistances to a liquid related occurrence.

BRIEF DESCRIPTION OF THE DRAWINGS

The foregoing and other features of the various embodiments of the incontinence detection system and detectors described herein will become more apparent from the following detailed description and the accompanying drawings in which.

DESCRIPTION

Figure 1:
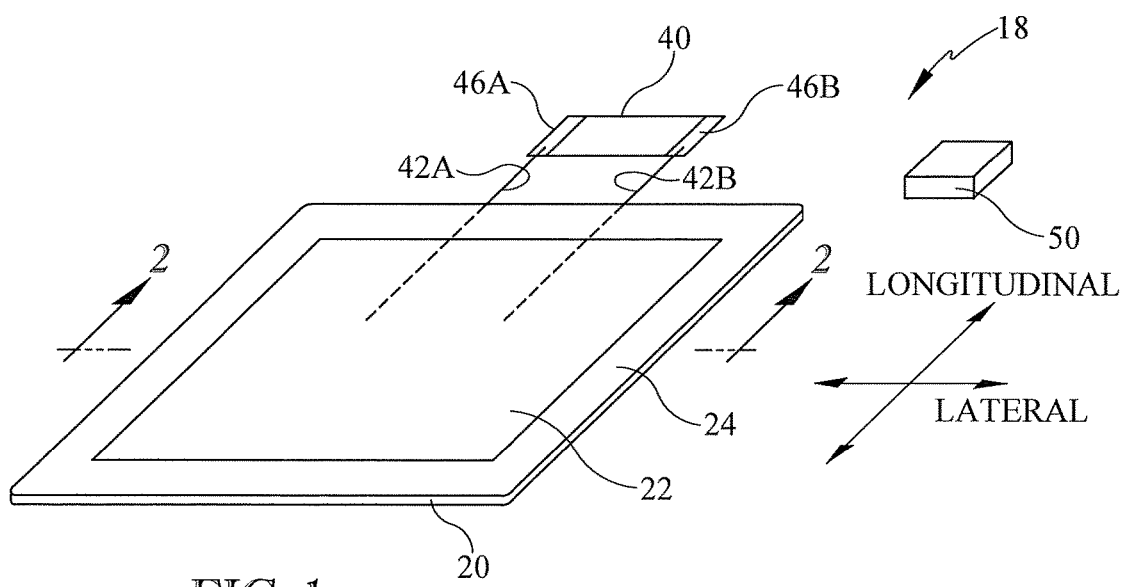
FIG. 1 is a schematic view of an incontinence detector in the form of a thin pad having a film layer and a sensing layer, and an accompanying RFID tag.

In this specification and drawings, features similar to or the same as features already described may be identified by reference characters or numerals which are the same as or similar to those previously used. Similar elements may be identified by a common reference character or numeral, with suffixes being used to refer to specific occurrences of the element. Dimensions are not necessarily to scale or in the proportions characteristic of an actual article; in particular thickness of the incontinence detector may be exaggerated to render certain details more easily discernible.

FIG. 1 shows an incontinence detector 18 in the form of a thin pad of material comprised of a film layer 20 and a sensing layer 22. The lateral and longitudinal dimensions of the sensing layer are smaller than the corresponding dimensions of the film layer so that the film layer defines a margin 24 around the sensing layer. The illustrated sensing layer is made of a nonwoven material, however a woven material having warp and weft fibers may also be satisfactory. Example nonwoven materials include drylaid material made by carding or airlaying, spunmelt material made by a spunlaid process or a meltblown process, wetlaid material, and flashspun material.

Figure 2:
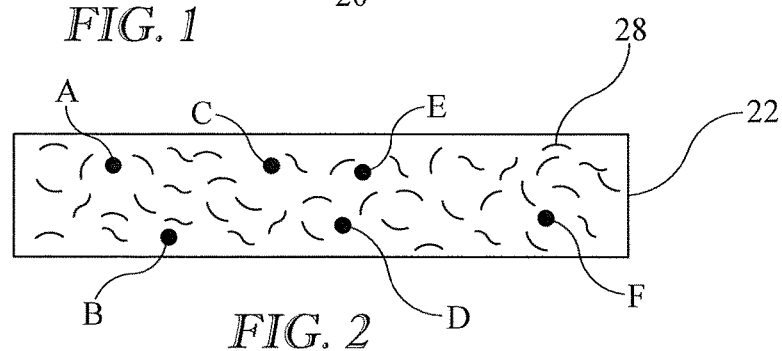
FIG. 2 is a view in the direction 2-2 of FIG. 1 showing electrically resistive elements uniformly distributed at a first density throughout the sensing layer of the pad.
Figure 3:
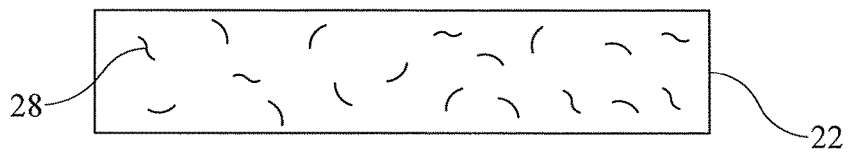
FIG. 3 is a view similar to FIG. 2 showing a lower density of the electrically resistive elements.

Referring additionally to FIGS. 2-3, the illustrated pad includes elements such as carbon fiber segments 28. Accordingly, material layer 22 may be referred to as a carbon fiber impregnated nonwoven material. The carbon fiber segments are uniformly distributed throughout layer 22 so that the carbon fiber density of the layer is spatially uniform. The phrase "carbon fiber density" is a measure of fibers per unit volume of material layer 22, not the density of the carbon fibers themselves. The fibers are electrically conductive, however they are intentionally distributed sparsely so that taken collectively they barely make a conductive path through the layer of material and therefore impart a relatively high baseline resistance (e.g. at least about 20 MΩ) to the layer. Therefore, elements 28 are referred to herein as electrically resistive elements, and layer 22 may be referred to as an electrically resistive layer. Because the fiber segments are uniformly distributed, the electrical resistance between any two points of layer 22 is proportional to the distance between those points. For example if distance AB equals distance CD then resistances $R_{AB}$ and $R_{CD}$ are equal. Similarly if distance EF is twice distance AB then $R_{EF}=2R_{AB}$.

Figure 4:
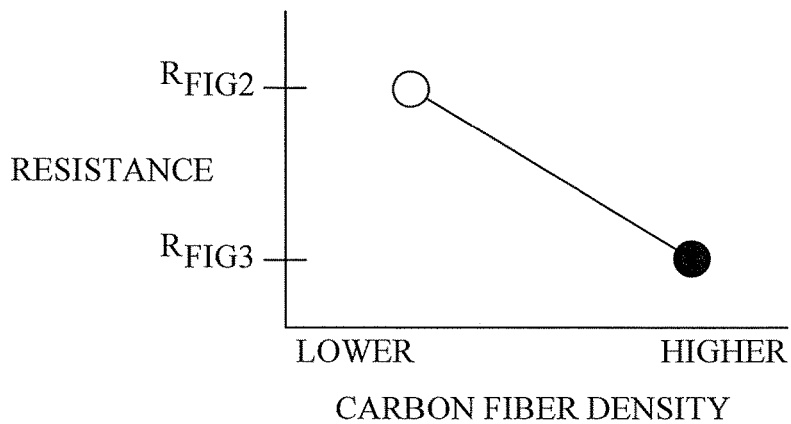
FIG. 4 is a graph showing that the electrical resistance of the pad varies inversely with density of the electrically resistive elements.

FIG. 4 is a graph of electrical resistance vs. carbon fiber density showing the baseline resistance of the material layers of FIGS. 2 and 3 (solid symbol and open symbol respectively) FIGS. 2-4 show that the carbon fiber density governs the electrical resistance in an inverse manner (although not necessarily linearly as shown) i.e. lower carbon fiber density provides a higher resistance and higher carbon fiber density provides a lower resistance. As discussed in more detail below, the material layer also has an actual electrical resistance which may or may not be the same as the baseline resistance.

The detector also includes an RFID tag 40. First and second leads 42A, 42B extend from terminals 46A, 46B of the tag and into material layer 22 without contacting each other. The illustrated RFID tag is a passive tag. An RFID reader 50 interrogates the tag and receives a return signal from the tag in response to the interrogation.

Figure 5:
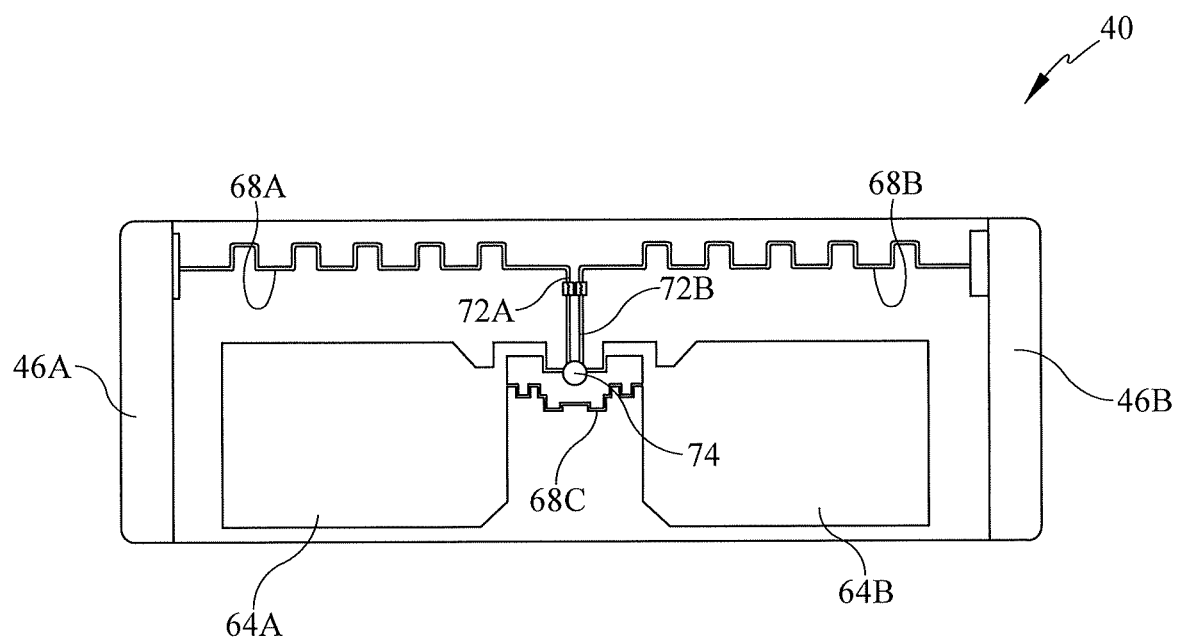
FIG. 5 is an plan view of an RFID tag suitable for use as the RFID tag of FIG. 1.
Figure 6:
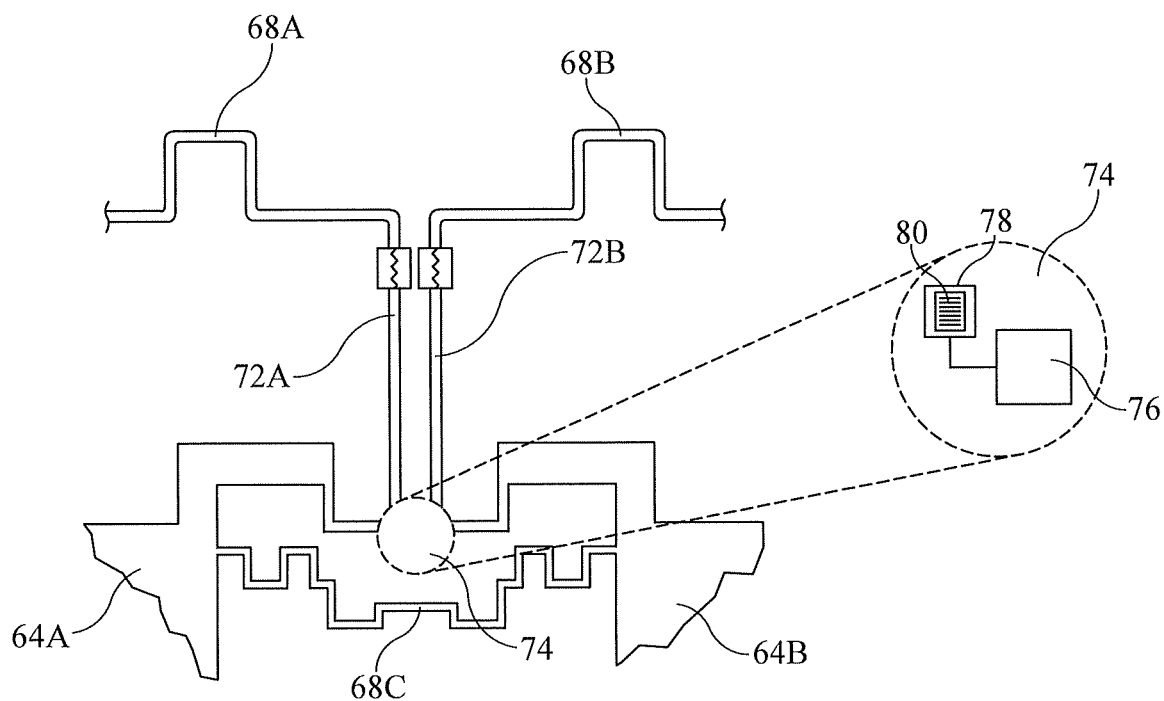
FIG. 6 is an enlarged view of a portion of the tag of FIG. 5.

Referring additionally to FIGS. 5-6, a suitable RFID tag 40 includes a pair of antenna ears 64A, 64B, first terminal 46A, second terminal 46B, a first undulating trace 68A extending from terminal 46A toward terminal 46B, a second undulating trace 68B extending from terminal 46B toward terminal 46A, and a third undulating trace 68C interconnecting ears 64A, 64B. Tamper input leads 72A, 72B extend from respective undulating traces 68A, 68B toward undulating trace 68C in spaced parallel relation with each other. Thus, lead 72A, undulating trace 68A, and terminal 46A, form one of the tamper inputs to an RFID chip 74, while lead 72B, undulating trace 68B, and terminal 46B, form the other of the tamper inputs to the RFID chip.

As seen most clearly in the inset of FIG. 6, the illustrated RFID chip 74 includes a processor 76 and a memory 78. The memory holds machine readable instructions 80 which the processor executes.

As noted above, the layer of material 22 has a baseline electrical resistance and an actual resistance. When the pad is dry the actual resistance equals the baseline resistance.

Accordingly, the baseline resistance is also referred to as the dry resistance. However when the layer of material is wet with an electrically conductive liquid, for example urine arising from an incontinence event, the actual resistance deviates from the baseline resistance. The actual resistance when the pad is wet is also referred to as its wet resistance. Because of the electrical conductivity of the liquid the wet resistance is less than the dry resistance.

Figure 7:
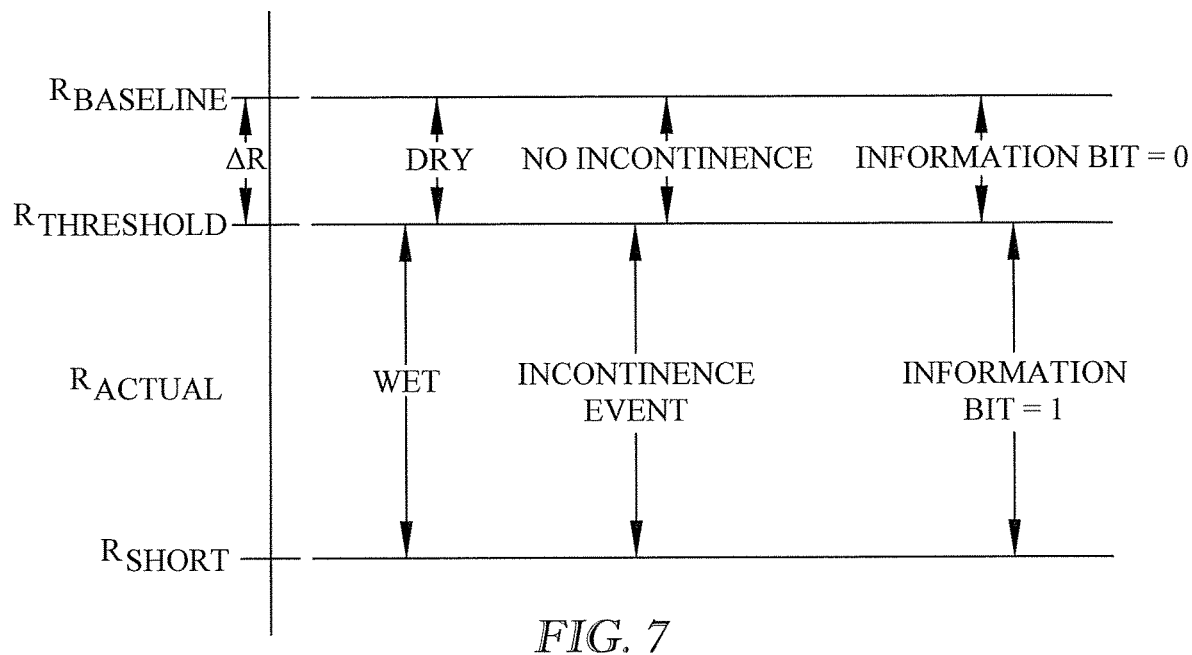
FIG. 7 is a chart showing how the actual electrical resistance of the pad correlates to pad condition (wet or dry), incontinence (no incontinence or occurrence of an incontinence even), and an information bit set by the RFID tag.

Referring to FIG. 7, an actual resistance substantially equal to the baseline resistance indicates that the pad is dry whereas a lower resistance (lower than a threshold resistance) indicates that liquid is present on the pad and is of sufficient volume to be considered an incontinence event. The RFID tag (in particular processor 76 acting according to instructions 80) is configured to be responsive to deviation of the actual resistance from the baseline resistance (which includes the limit case of zero deviation). More specifically, processor 76 evaluates the electrical resistance relative to the baseline resistance thereby causing the tag to be responsive to deviation of the actual resistance from the baseline resistance. In other words the processor responds in a first way to the dry electrical resistance and responds in a second way to the wet electrical resistance. In one specific embodiment the tag responds by setting an information bit to one value (e.g. 0) when the actual resistance of material layer 22 is higher than a given threshold resistance, and to the opposite value (1) when the actual resistance of material layer 22 is lower than the threshold. As used herein the action of setting a bit to a value includes allowing the bit to remain at its existing value if the existing value is consistent with actual resistance in comparison to the baseline resistance. The sensitivity of the detector to the presence of liquid is governed at least in part by the difference $\Delta R$ between the baseline resistance and the threshold resistance.

In practice, interrogator 50 periodically interrogates the RFID tag. The tag responds with a return signal whose information content depends on the resistance of material layer 22, for example as indicated by the polarity of the information bit. Accordingly, the information content of the return signal reveals whether the pad is dry (an incontinence event has not occurred) or wet (an incontinence event has occurred). One example of a return signal is a signal that causes a warning light to turn on if incontinence is detected. Another example is a signal which causes a display at a nurses' station to display the wet/dry status of the pad. Another example is a signal that reports the wet/dry status of the pad to an electronic medical record.

In summary, absorption of liquid by layer of material 22 causes the actual resistance of the material to deviate from its baseline resistance. In other words the actual electrical resistance of layer 22 is influenced by the presence of liquid in the layer. The processor responds with an indication of whether or not a liquid is present in the layer. Additionally or alternatively the machine readable instructions may be written so that the processor responds with an indication of the identity of the liquid, or at least an indication narrowing down the identity of the liquid to one of two or more candidate liquids. The identity indication is based on the electrical conductivity of the liquid.

Figure 8:
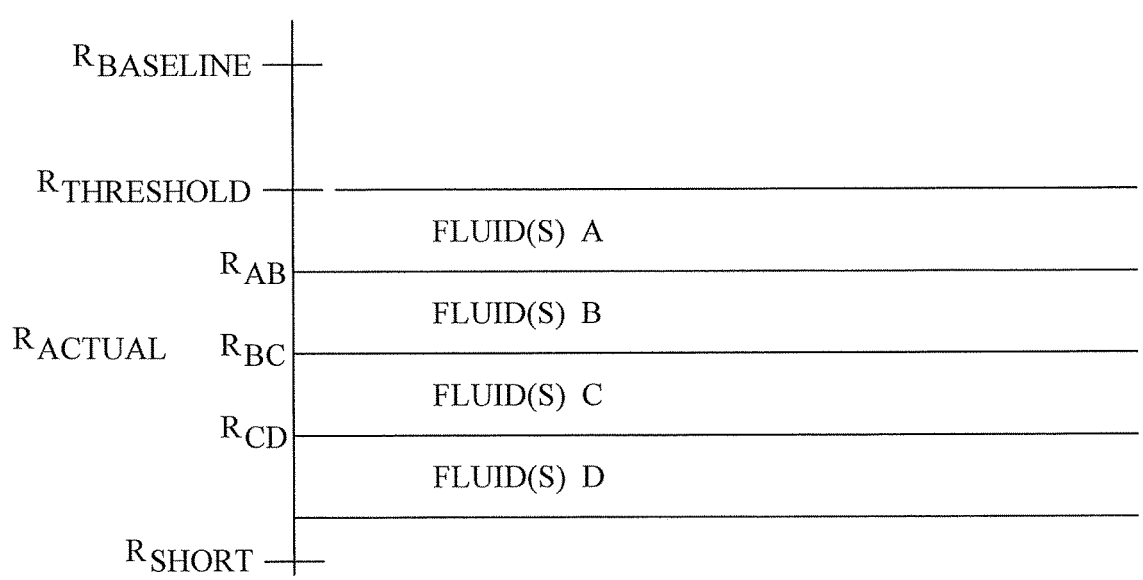
FIG. 8 is a chart showing how the actual electrical resistance of the pad may be used to distinguish between different liquids or different classes of liquids.

FIG. 8 illustrates distinguishing among liquids of different identities. An actual resistance in the range of $R_{THRESHOLD}$ to $R_{AB}$ indicates the presence of a liquid (liquid A) or the presence of one of two or more candidate liquids (liquids in a liquid set A). Similarly, other liquids having higher electrical conductivity cause the resistance of layer 22 to fall within one of the other illustrated resistance bands. Operation of the incontinence detector as shown in FIG. 8 may enable the detector to distinguish between, for example, urine, loose feces, vomit, perspiration, and so forth. In connection with distinguishing among liquids of different identities, the resistance band from $R_{THRESHOLD}$ to $R_{BASE-LINE}$ is interpreted as corresponding to a liquid whose identity is "none", i.e. no liquid is present.

Figure 9:
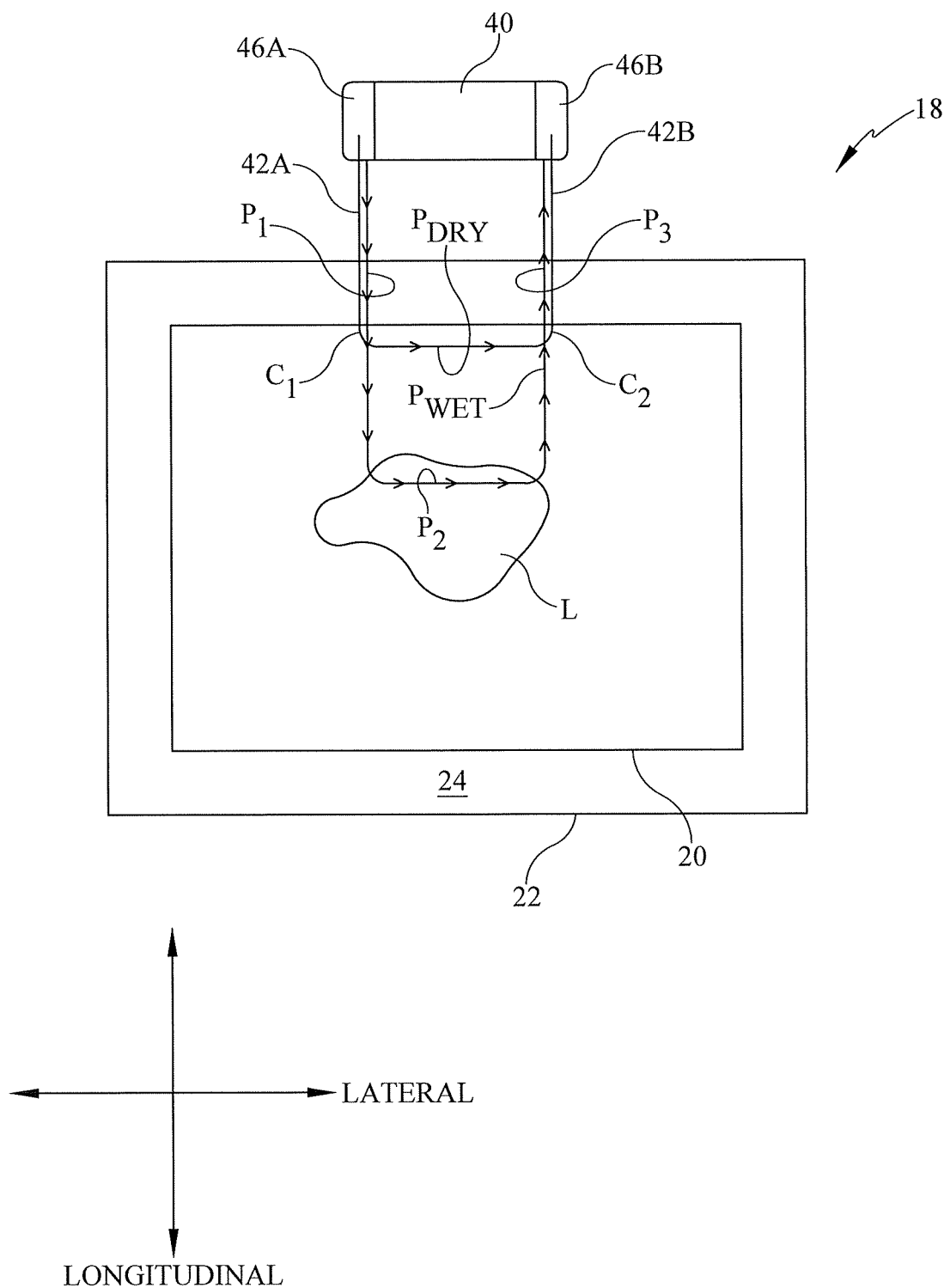
FIG. 9 is a schematic plan view of a representative incontinence detector illustrating the concept of ensuring that when liquid is present the electrical path between terminals of the RFID tag passes through the liquid.

One of the design considerations of the above described detector is to ensure that when liquid is present the electrical path from terminal 46A to terminal 46B passes through the liquid L. This is shown conceptually and schematically in FIG. 9. Electrical path $P_{WET}$ is illustrated as three path portions $P_1$, $P_2$, $P_3$. Path portion $P_1$ extends between terminal 46A and liquid L and has a resistance $R_1$. Path portion $P_2$ is the portion of the path that traverses the liquid. Path portion $P_2$ has a resistance $R_2$. Path portion $P_3$ extends between liquid L and terminal 46B and has a resistance $R_3$. Taken together, path portions $P_1$, $P_2$ and $P_3$ extend between terminals 46A and 46B. Path portion $P_{DRY}$ also extends between terminals 46A and 46B but bypasses the liquid and has a resistance $R_4$. Provided the sum of $R_1$, $R_2$, and $R_3$ is less than the sum of $R_4$, the electrical flow path passes through the liquid. Therefore, the design constraint is:

$$(R1+R2+R3)<R4 \tag{1}$$

Because the distribution of the resistive elements 28 is spatially uniform, the resistance of dry material layer 22 is proportional to path length through the material. Accordingly a larger spacing between points $C_1$, $C_2$ where leads 42A, 42B contact the sensing layer of the pad is more satisfactory than a smaller spacing.

Figure 10:
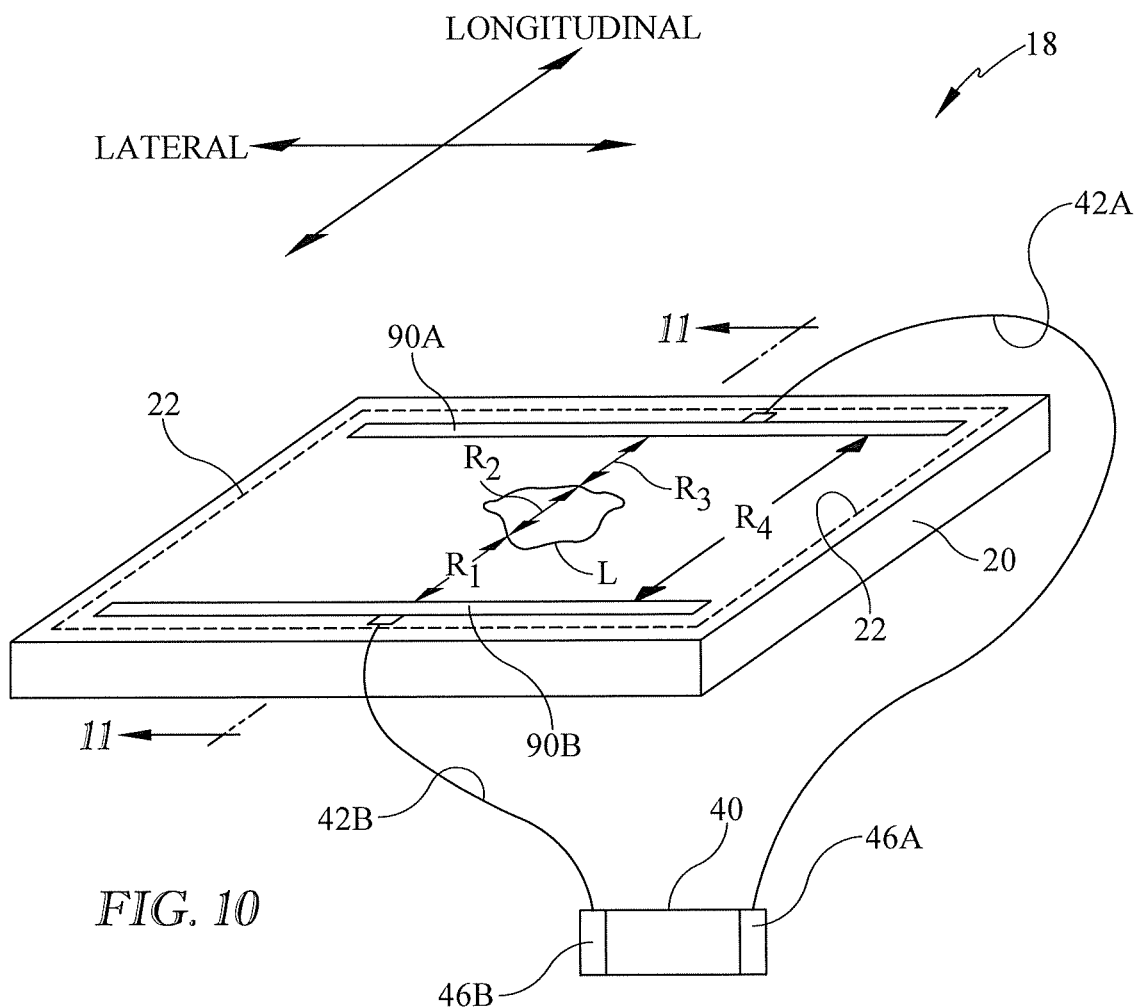
FIG. 10 is a schematic perspective view of the incontinence detector (with the planform of the sensing layer shown in phantom) showing a first example of carrying out the concept of FIG. 9.
Figure 11:
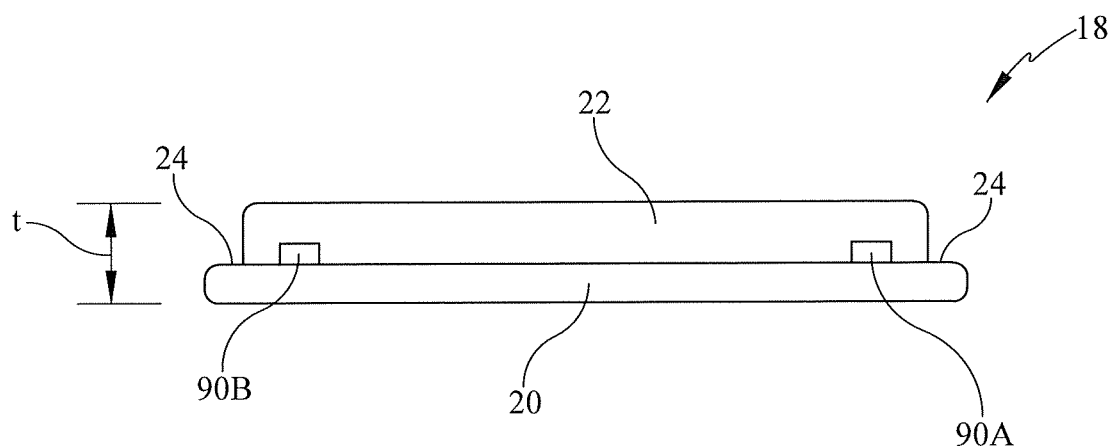
FIG. 11 is a schematic cross sectional view in the direction 11-11 of FIG. 10.

FIGS. 10-16 show examples of achieving satisfactory spacing. In the arrangement of FIGS. 10-11, first and second pad traces 90A, 90B are printed onto the film layer 20 along opposite edges of the layer. Sensing layer 22 overlies the traces and most of the film layer. Leads 42A, 42B connect pad traces 90A, 90B to RFID tag 40. The RFID tag is illustrated as off-board the pad but could instead be an on-board tag. The condition of equation (1) is satisfied.

Figure 12:
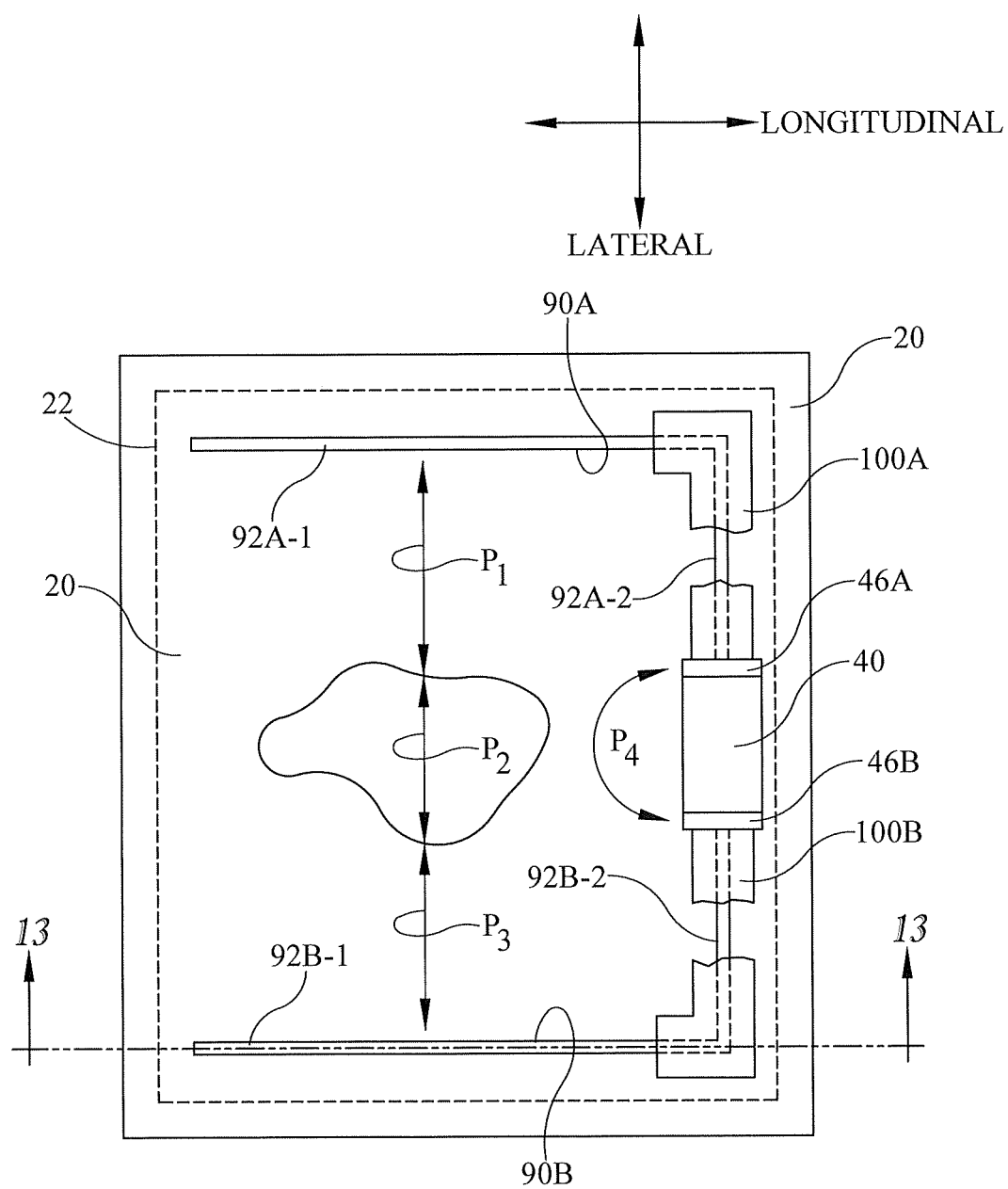
FIG. 12 is a schematic plan view of the incontinence detector (with the planform of the sensing layer shown in phantom) showing a second example of carrying out the concept of FIG. 9.
Figure 13:
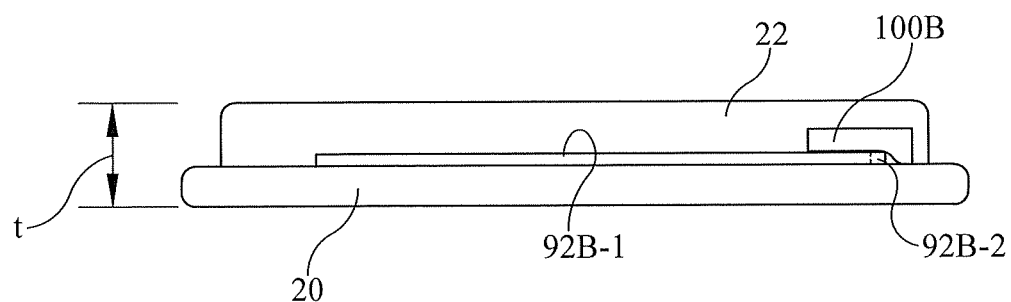
FIG. 13 is a schematic view in the direction 13-13 of FIG. 12 with pad thickness t exaggerated in the interest of clarity.

Turning now to the arrangement of FIGS. 12-13 a first trace 90A is printed on the film layer 20 so that the first trace includes a longitudinally extending segment 92A-1 extending longitudinally alongside a first edge of the film layer and a laterally extending segment 92A-2 extending laterally alongside a third edge of the layer. A second trace 90B is printed on the film layer 20 so the second trace includes a longitudinally extending segment 92B-1 extending longitudinally alongside a second edge of the film layer and a laterally extending segment 92B-2 extending laterally alongside the third edge of the layer. Segments 92A-2 and 92B-2 are each connected to respective terminals 46A, 46B of an RFID tag 40. An electrical insulating strip 100A, 100B covers segments 92A-2 and 92B-2. (A portion of each insulating strip is broken away to reveal part of each trace segment 92A-1 and 92A-2.) As a result the electrical resistance of short path $P_4$ is greater than the series resistance of paths $P_1$, $P_2$, and $P_3$, and the condition of equation (1) is satisfied.

Figure 14:
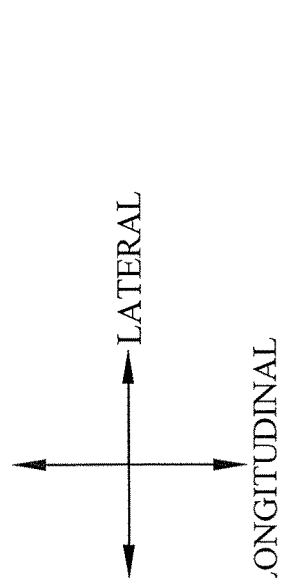
FIG. 14 is a schematic plan view of the incontinence detector (with the planform of the sensing layer shown in phantom) showing a third example of carrying out the concept of FIG. 9.
Figure 14:
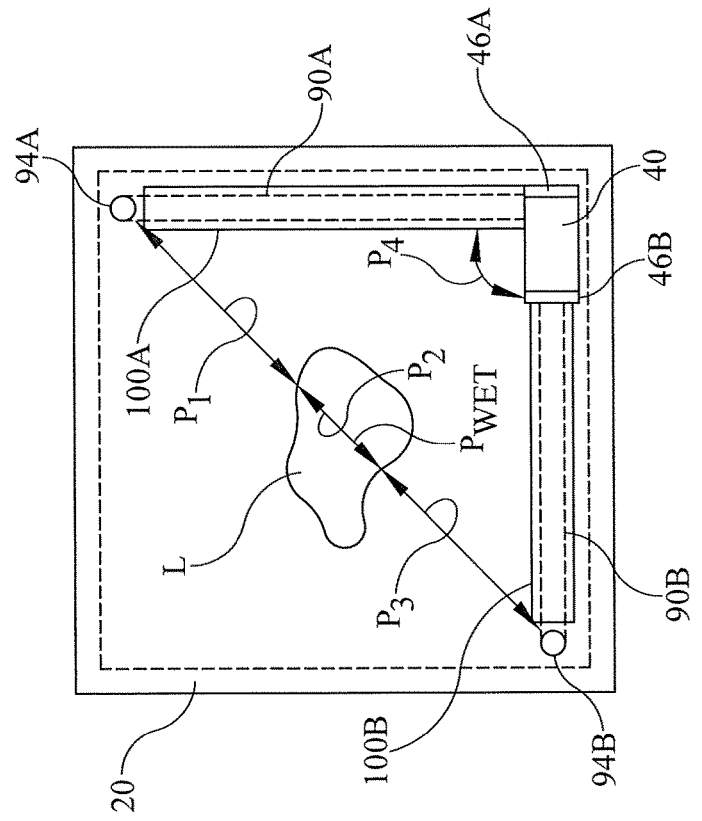
Figure 15:
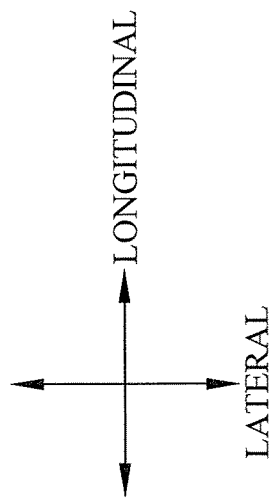
FIG. 15 is a schematic plan view of the incontinence detector (with the planform of the sensing layer shown in phantom) showing a fourth example of carrying out the concept of FIG. 9.
Figure 15:
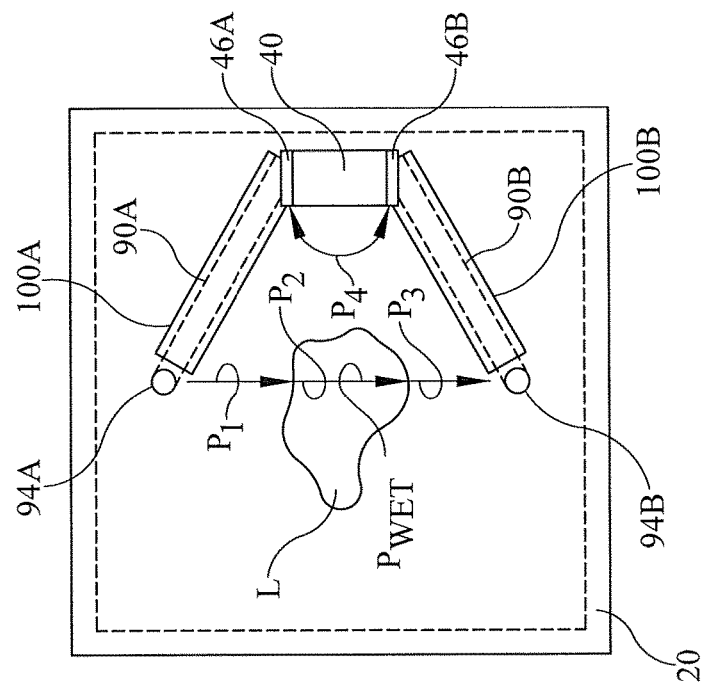

In the arrangement of FIGS. 14-15 each trace 90A, 90B is printed on film layer 20. Each trace is connected to a terminal 46A, 46B of RFID tag 40. Insulating strips 100A, 100B cover traces 90A, 90B except at the end of each trace remote from RFID tag 40. Those remote ends are left uncovered by insulation and therefore define terminals 94A, 94B which are in contact with the overlying (and unillustrated) sensing layer 22. Due to the insulation the electrical resistance of short path $P_4$ is greater than the series resistance of paths $P_1$, $P_2$, and $P_3$, and the condition of equation (1) is satisfied.

Figure 16:
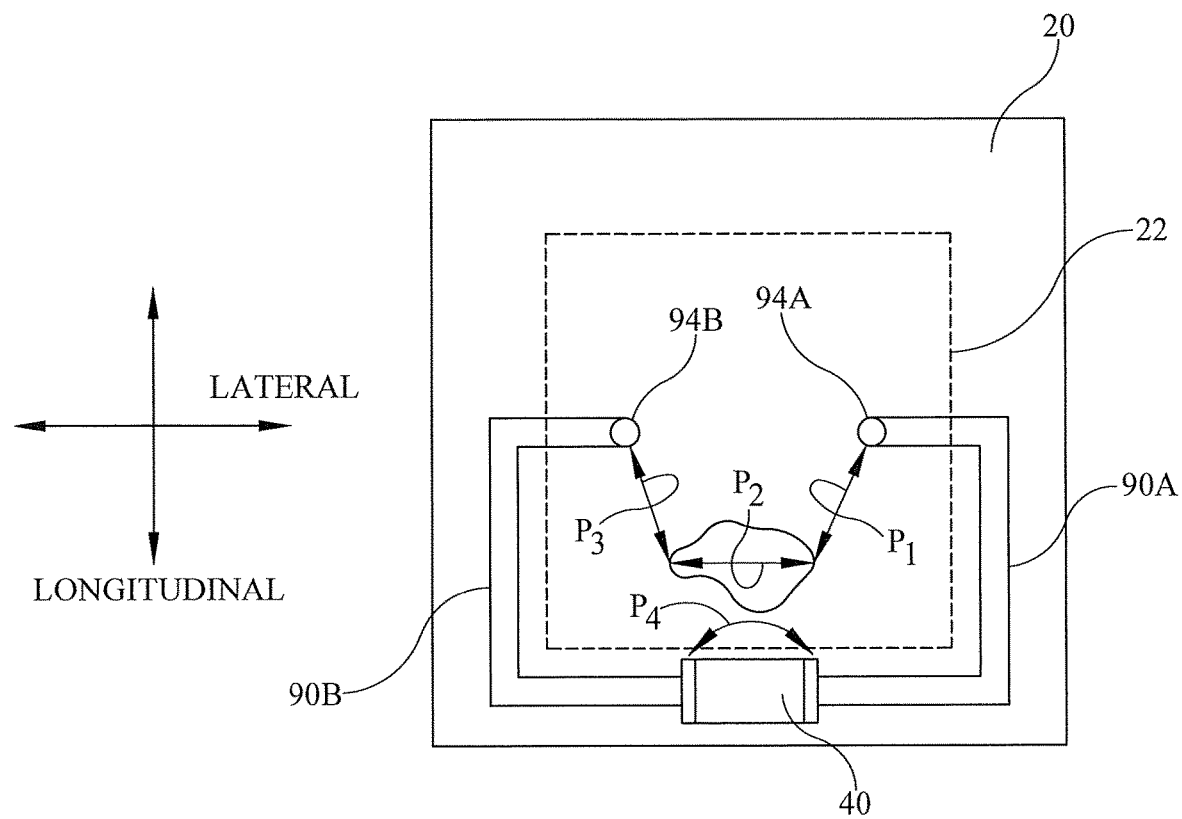
FIGS. 16-17 are schematic plan views of the incontinence detector showing fifth and sixth examples of carrying out the concept of FIG. 9.

FIG. 16 shows an embodiment in which RFID tag 40 resides on film layer 20 and most or all of traces 90A, 90B are printed on the film layer. The traces extend along the film layer to terminals 94A, 94B, which are in contact with sensing layer 22. Electrical path $P_{WET}$ is illustrated as three path portions: $P_1$ extending from terminal 94A to liquid L, $P_2$ traversing the liquid, and $P_3$ extending from the liquid L to terminal 94B. Because the film is not conductive, the electrical resistance of short path $P_4$ is greater than the series resistance of paths $P_1$, $P_2$, and $P_3$, and the condition of equation (1) is satisfied.

Figure 17:
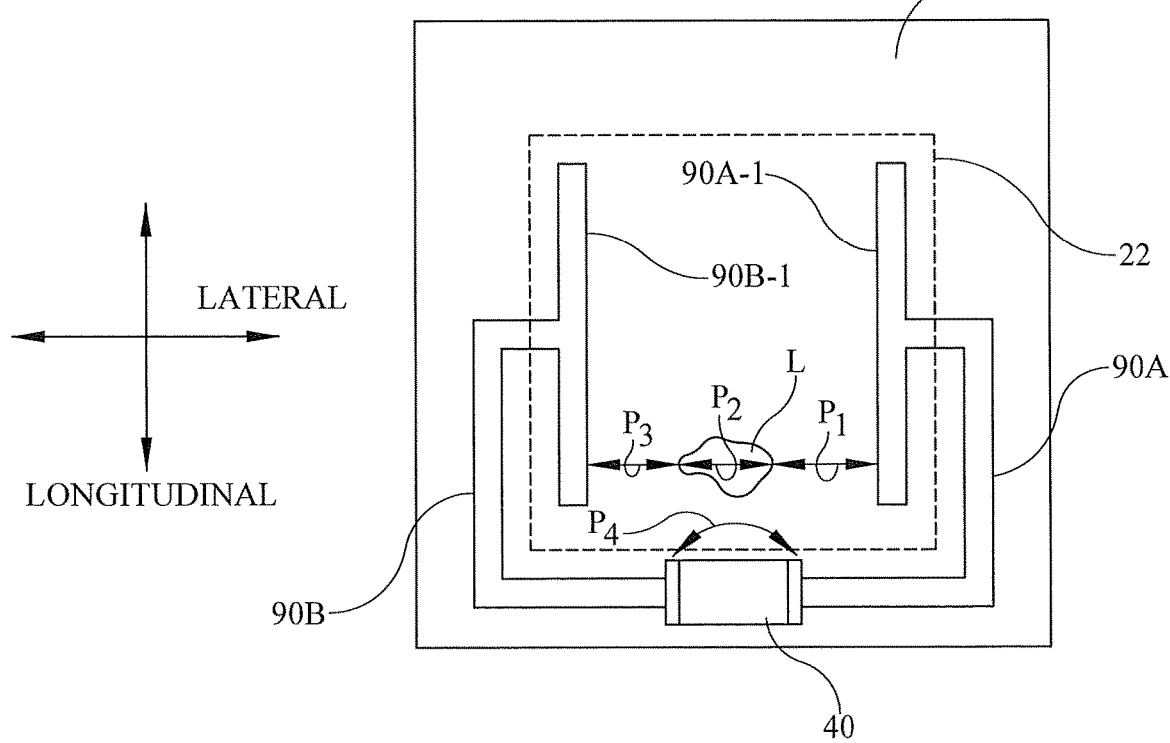

FIG. 17 shows an arrangement similar to that of FIG. 16 in which each trace 90A, 90B has a portion 90A-1, 90B-1 which extends along sensing layer 22. Alternatively, portions 90A-1, 90B-1 can be thought of as spatially extended variants of terminals 94A, 94B of FIG. 16. Because film 20 is not conductive, the electrical resistance of short path $P_4$ is greater than the series resistance of paths $P_1$, $P_2$, and $P_3$, and the condition of equation (1) is satisfied.

Figure 18:
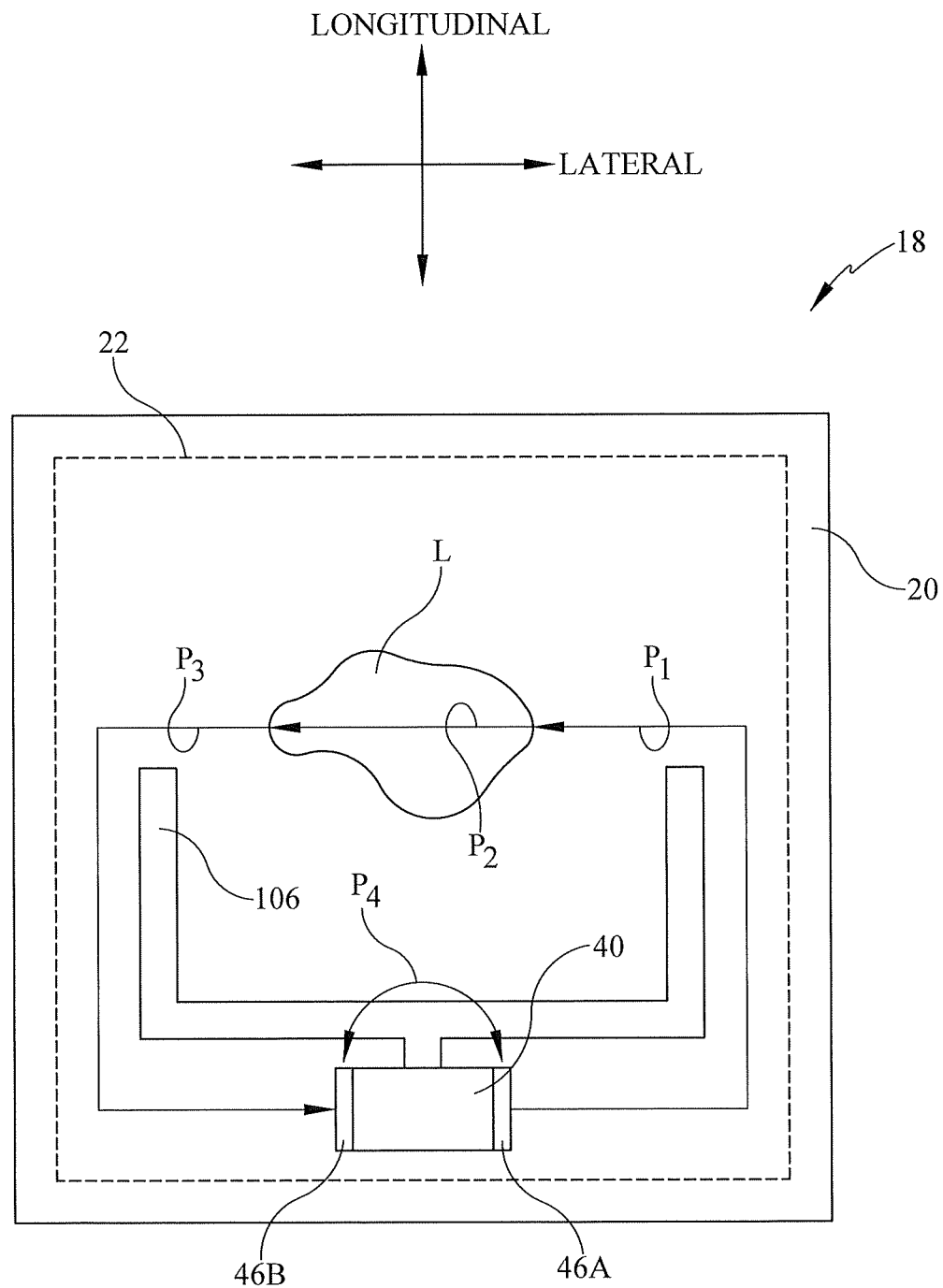
FIG. 18 is a schematic plan view of the incontinence detector showing a seventh example of carrying out the concept of FIG. 9.

FIG. 18 shows an arrangement in which a full thickness U-shaped portion 106 of the carbon fiber impregnated material has been removed. Tag terminals 46A, 46B are connected directly to material layer 22. Due to the absence of conductive material at 106, the electrical resistance of short path $P_4$ is greater than the series resistance of paths $P_1$, $P_2$, and $P_3$, and the condition of equation (1) is satisfied.

Figure 19:
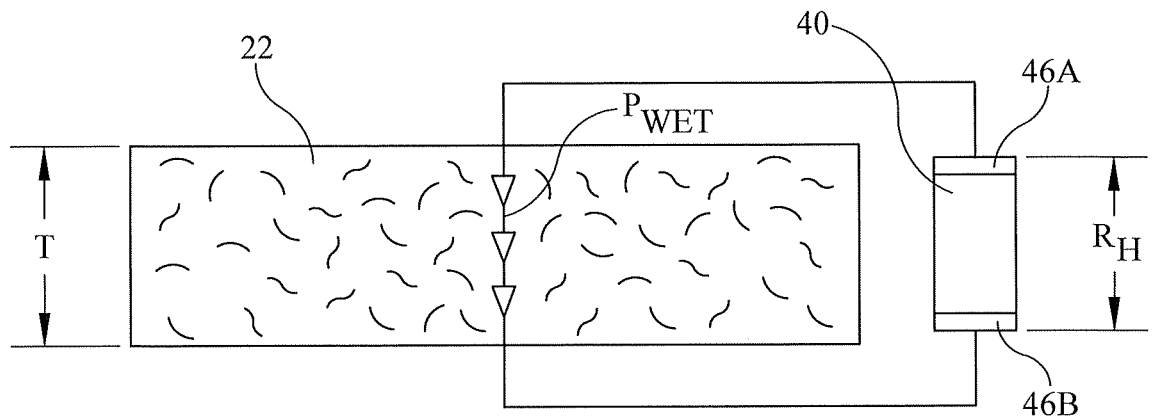
FIGS. 19-21 are elevation views of the sensing layer of an incontinence pad illustrating a pad with different amounts of liquid present or, alternatively, different penetration depths of the liquid.
Figure 20:
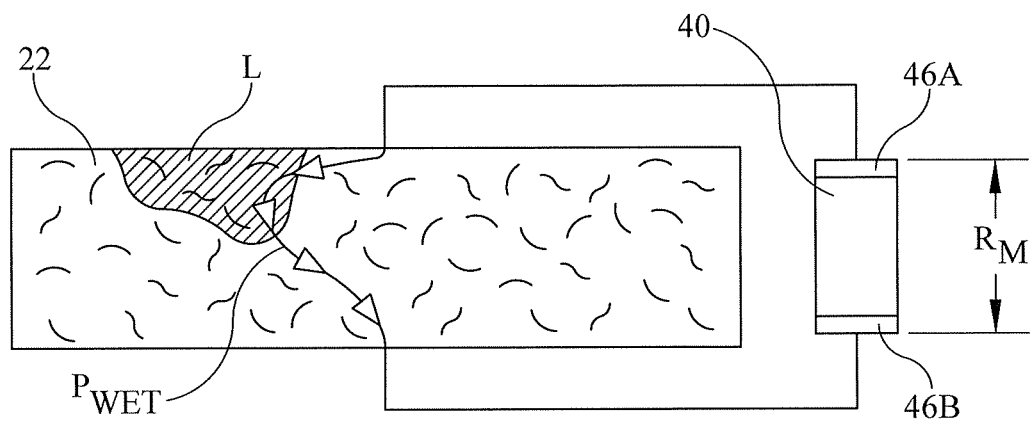
Figure 21:
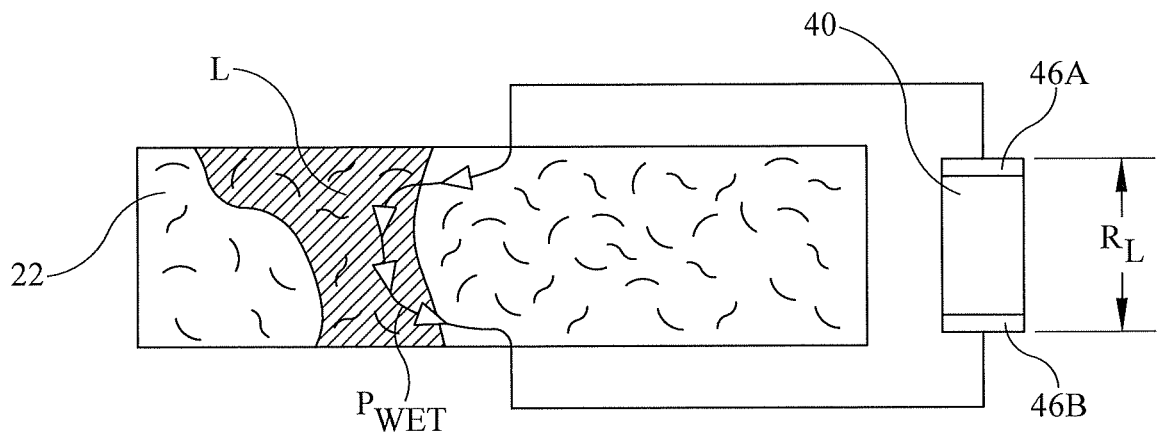
Figure 22:
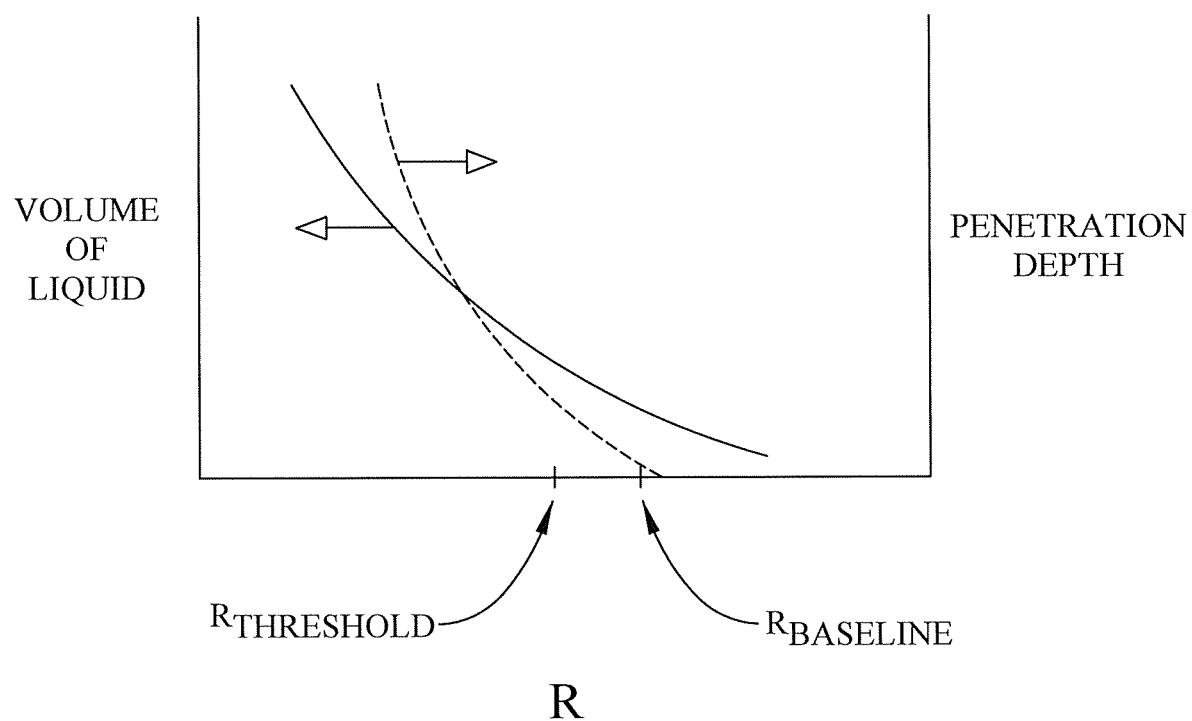
FIG. 22 is a graph showing how the resistance of the pad of FIGS. 19-21 may be interpreted as an indicator of volume of liquid (solid line) or penetration depth (dashed line).

The pad as described and contemplated above is thin enough that any meaningful amount of liquid will soak completely through the pad and will do so in a short time, for example no more than several seconds. FIGS. 19-21 show a material layer 22 with a thickness T large enough that only larger volumes of a liquid will soak completely through the pad. Smaller volumes of liquid may soak into the pad but not through it. The RFID tag 40 is connected across the thickness dimension T of the pad. When the material layer is dry (FIG. 19) the resistance across the tag terminals is a high resistance $R_H$. When a moderate volume of liquid L is present it may soak into the material layer, but not completely through the layer as seen in FIG. 20. Accordingly the resistance across the tag terminals is $R_M$, a medium resistance lower than $R_H$. When liquid is present in a large enough volume to soak through the material layer as seen in FIG. 21, the resistance across the tag terminals is $R_L$, a low resistance less than $R_M$. FIG. 22 illustrates how the resistance may be interpreted as an indicator of volume of liquid (solid line) or penetration depth (dashed line).

Figure 23:
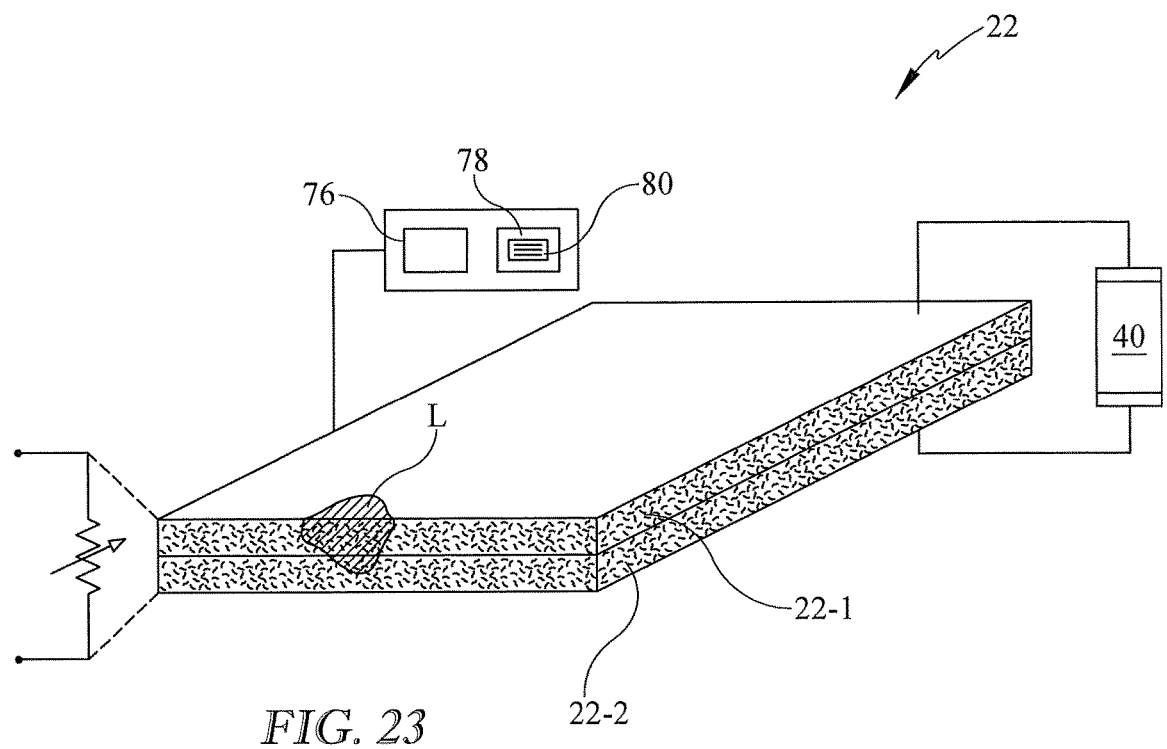
FIG. 23 is a view of an incontinence detector pad having multiple sensing layers.

FIG. 23 shows a multilayer incontinence detector and a schematic of an electrical circuit analogue. Detector sensing layer 22 includes a first layer of material 22-1 having a first baseline electrical resistance, and a second layer of material 22-2 having a second baseline electrical resistance which differs from the first baseline electrical resistance. Additional layers may be provided if desired. The material layers may be a nonwoven material impregnated with resistive elements, such as carbon fiber elements, as already described. As illustrated, liquid L, which has been deposited on first layer 22-1, has penetrated through first layer 22-1 and part way through second layer 22-2.

Figure 24:
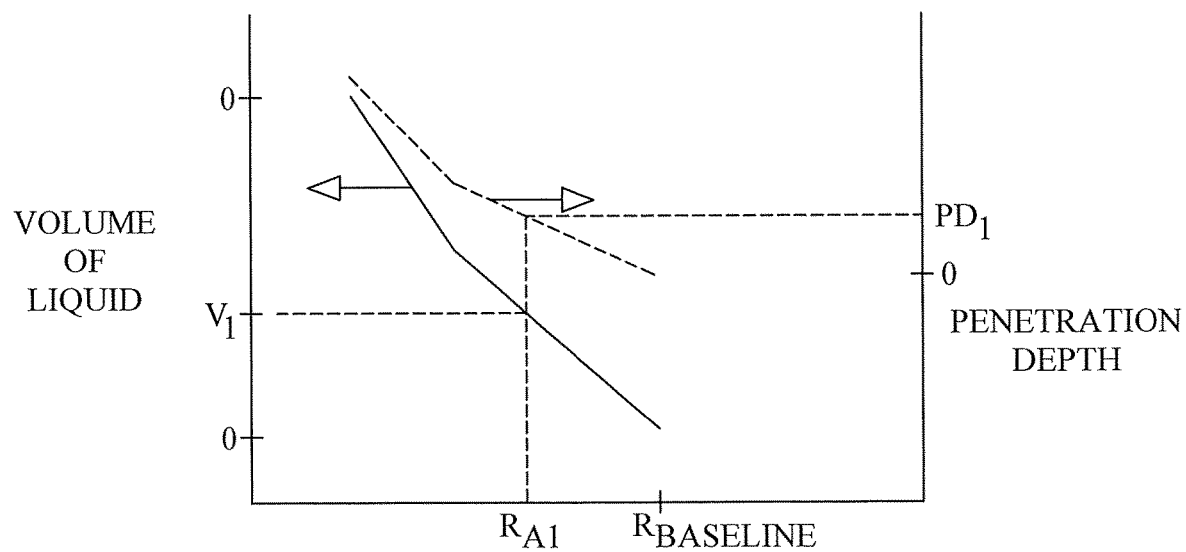
FIG. 24 is a graph illustrating how the actual resistance of the pad of FIG. 23 may be interpreted as an indicator of volume of liquid (solid line) or liquid penetration depth (dashed line).

The baseline resistance of each layer 22-1, 22-2 is its actual resistance when dry. When wet with a conductive liquid, each layer exhibits an actual resistance which deviates from its baseline resistance. This is reflected in the circuit schematic by the variable resistor (which could alternatively and equivalently be illustrated by two variable resistors in series, one resistor for each layer). FIG. 24 illustrates how the resistance may be interpreted as an indicator of volume of liquid (solid line) or penetration depth (dashed line). In the example given in FIG. 24 the actual resistance $R_{A1}$ corresponds to a liquid volume $V_1$ and/or a penetration depth $P_{D1}$.

Figure 25:
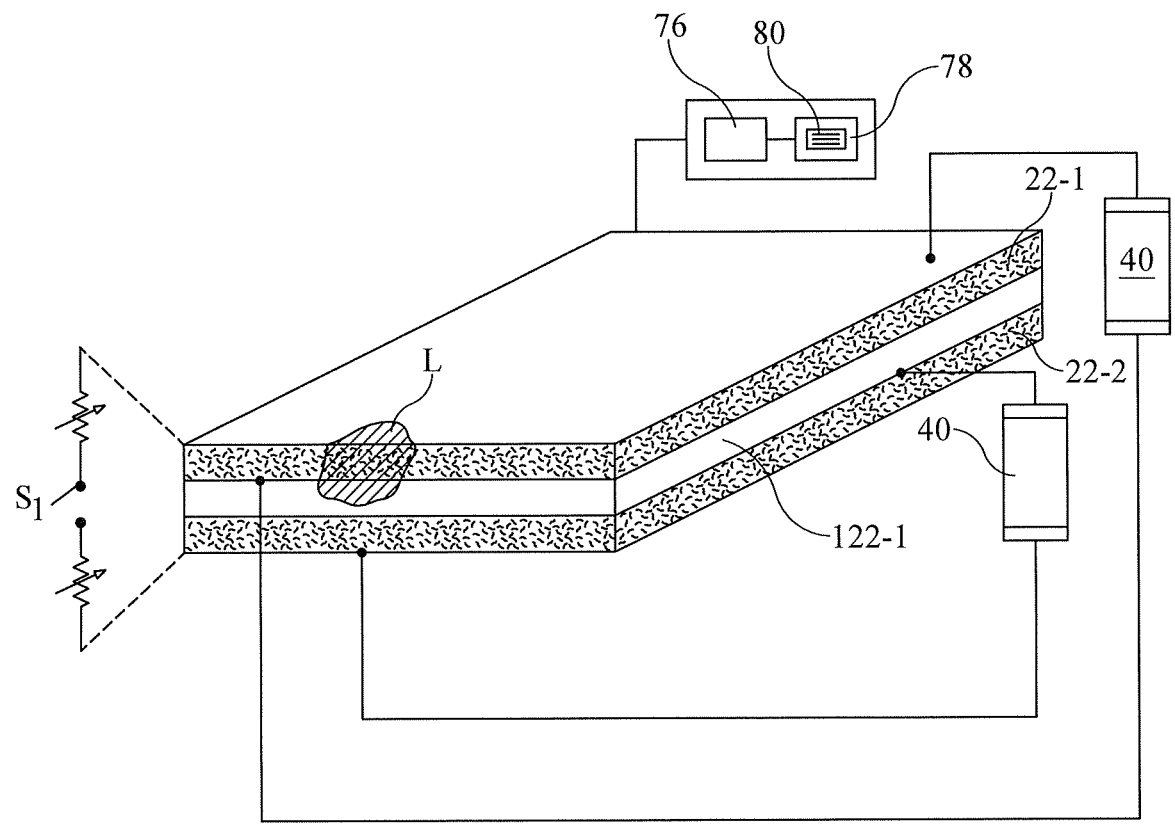
FIGS. 25-26 are views of another multi-layer incontinence detector pad having electrically resistive material layers alternating with intermediate layers.

FIG. 25 shows a another multilayer incontinence detector and a schematic of an electrical circuit analogue. The detector includes a first layer of material 22-1 having a first baseline electrical resistance, and a second layer of material 22-2 having a second baseline electrical resistance which may or may not be equal to the first baseline resistance. The material layers may be a nonwoven material impregnated with resistive elements, such as carbon fiber elements, as already described. The detector also includes a first intermediate layer 122-1 separating the first layer from the second layer. The intermediate layer is not electrically conductive. In one embodiment the intermediate layer is a woven or nonwoven absorbent layer. As illustrated, liquid L which has been deposited on first layer 22-1 has penetrated through first layer 22-1 and part way through first intermediate layer 122-1.

The baseline resistance of each layer 22-1, 22-2 is its actual resistance when dry. When wet with a conductive liquid, each layer exhibits an actual resistance which deviates from its baseline resistance. This is reflected in the circuit schematic by the variable resistors. The electrical schematic represents the nonconductive intermediate layer as switch $S_1$. Switch $S_1$ is shown as open because the liquid has not penetrated through intermediate layer 122-1 and overcome its nonconductivity.

Figure 26:
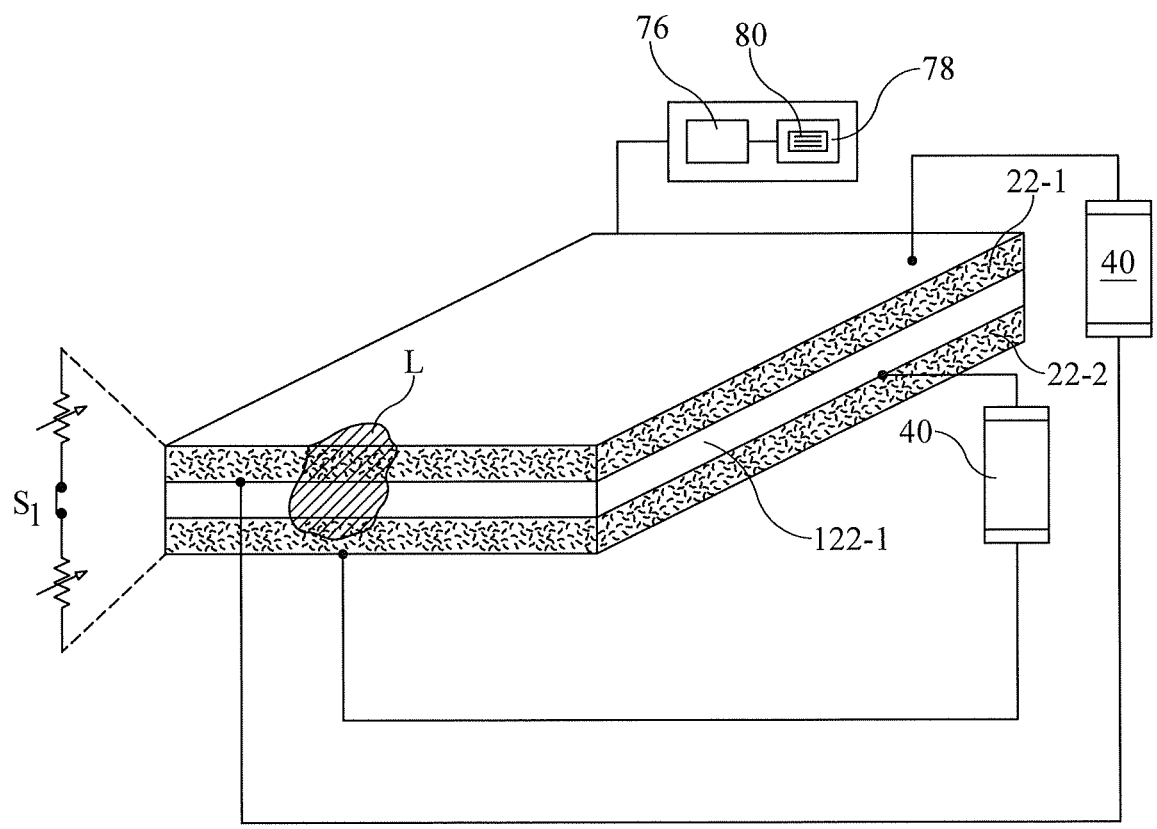

FIG. 26 is the same as FIG. 25 except that in FIG. 26 Liquid L has penetrated completely through intermediate layer 122-1 and into but not completely through material layer 22-2. Switch $S_2$ is shown as closed because penetration of liquid L through intermediate layer 122-1 has imparted some degree of electrical conductivity to that otherwise nonconductive layer.

The detector also includes a processor 76 and machine readable instructions 80. When the processor operates according to the instructions it responds by relating the actual resistances, in comparison to the baseline resistances, to a liquid related occurrence (including the limit case of a null occurrence corresponding to the absence of liquid).

One example of a liquid related occurrence which can be signified by the resistances is the presence of a particular volume or quantity of a liquid, including the limit case of no liquid. For example the resistances can be interpreted as an indicator that the detector is oriented with the second layer vertically below the first layer and as an indicator of how much liquid is present as set forth in table 1.

TABLE 1

| Actual Resistance of First Layer | Actual Resistance of Second Layer | Interpretation |
|---|---|---|
| Baseline | Baseline | No Liquid Present |
| Less than baseline | Baseline | Small amount of liquid present |
| Less than baseline | Less than baseline | Large amount of liquid present |

A second example of a liquid related occurrence which can be signified by the resistances is the spatial distribution of the liquid. For example the resistances can be interpreted as an indicator that the detector is oriented with the second layer vertically below the first layer and as an indicator of the distribution of the liquid as set forth in table 2.

TABLE 2

| Actual Resistance of First Layer | Actual Resistance of Second Layer | Interpretation |
| --- | --- | --- |
| Baseline | Baseline | No Liquid Present |
| Less than baseline | Baseline | Liquid is present predominantly at the first layer |
| Less than baseline | Less than baseline | Liquid is present predominantly at the first and second layers |

A third example of a liquid related occurrence which can be signified by the resistances is the severity of an incontinence event (including the limit case of no incontinence). For example the resistances can be interpreted as an indicator that the detector is oriented with the second layer vertically below the first layer and and as an indicator of the severity of an incontinence event as set forth in table 3.

TABLE 3

| Actual Resistance of First Layer | Actual Resistance of Second Layer | Interpretation |
| --- | --- | --- |
| Baseline | Baseline | An incontinence event has not occurred. |
| Less than baseline | Baseline | A minor incontinence event has occurred |
| Less than baseline | Less than baseline | A major incontinence event has occurred |

Figure 27:
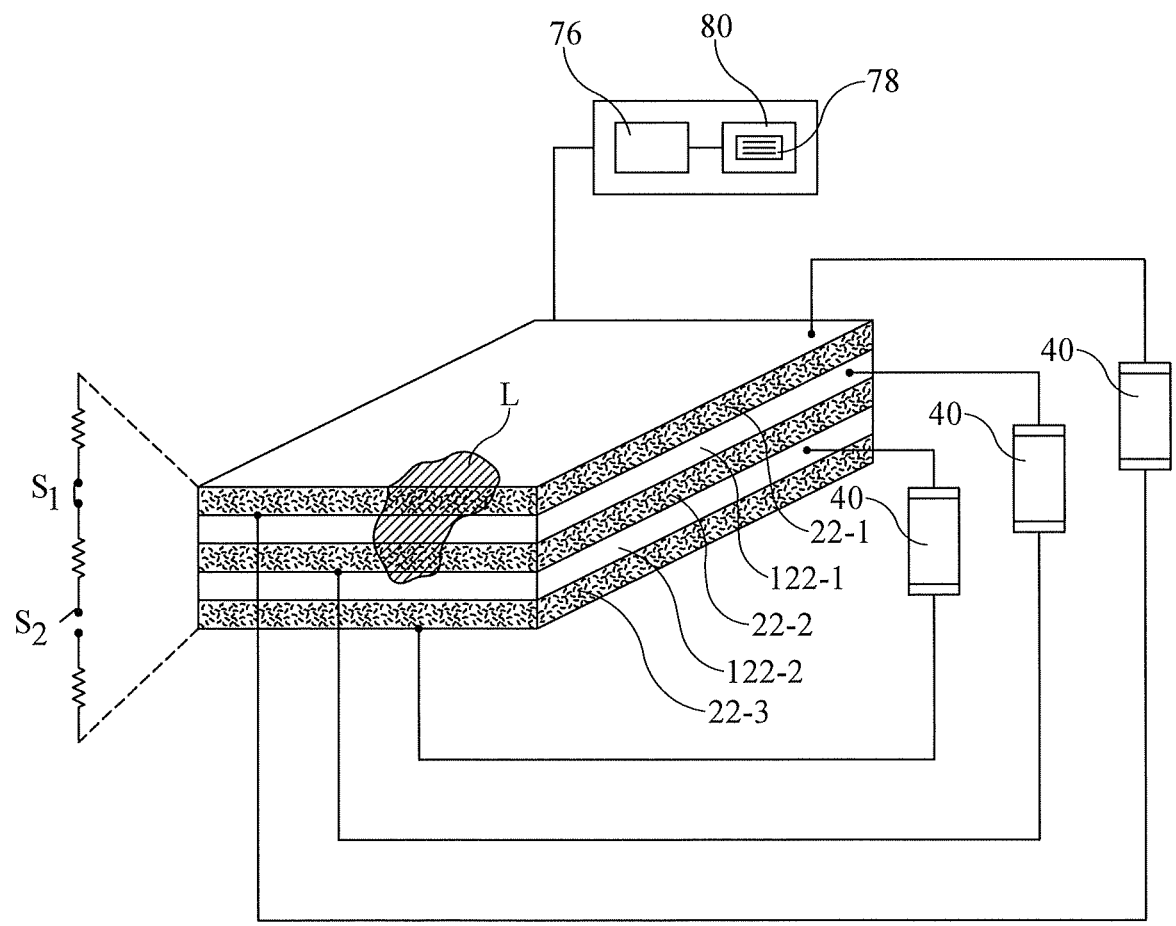
FIG. 27 is a view similar to that of FIG. 25 showing a multilayer incontinence detector with N material layers (N≥2) alternating with M intermediate layers and a schematic of an electrical circuit analogue.

FIG. 27 is a view similar to that of FIG. 25 showing a more general embodiment of a multilayer incontinence detector and a schematic of an electrical circuit analogue. In general the incontinence detector includes N sensing layers 22 (N≥2) and M intermediate layers (M=N−1) arranged so that the sensing layers 22 and the intermediate layers 122 alternate with each other. The illustration shows the specific case where N=3 and M=2. The detector includes a first layer of material 22-1 having a first baseline electrical resistance, a second layer of material 22-2 having a second baseline electrical resistance, and a third layer of material 22-3 having a third baseline resistance. The baseline resistances need not be equal to each other. The material layers may be a nonwoven material impregnated with resistive elements, such as carbon fiber elements, as already described. The detector also includes a first intermediate layer 122-1 separating the first layer from the second layer and a second intermediate layer 122-2 separating the second layer from the third layer. The intermediate layers are not inherently electrically conductive. In one embodiment the intermediate layer is a woven or nonwoven absorbent layer. As illustrated, liquid L which has been deposited on first layer 22-1 has penetrated completely through first layer 22-1, intermediate layer 122-1 and second layer 22-2. The liquid has penetrated into but not through second intermediate layer 122-2.

The baseline resistance of each layer 22-1, 22-2, 22-3 is its actual resistance when dry. When wet with a conductive liquid, each layer exhibits an actual resistance which deviates from its baseline resistance. This is reflected in the circuit schematic by the variable resistors. The electrical schematic represents the nonconductive intermediate layer 122-1 as switch $S_1$ and the nonconductive intermediate layer 122-2 as switch $S_2$. Switch $S_1$ is shown as closed because the liquid has penetrated through layer 122-1 and into layer 22-2. Switch $S_2$ is shown as open because the liquid has not penetrated through intermediate layer 122-1 and overcome its nonconductivity.

The detector also includes a processor 76 and machine readable instructions 80. When the processor operates according to the instructions it responds by relating the actual resistances, in comparison to the baseline resistances, to a liquid related occurrence (including the limit case of a null occurrence corresponding to the absence of liquid).

One example of a liquid related occurrence which can be signified by the resistances is the presence of a particular volume or quantity of a liquid, including the limit case of no liquid. For example the resistances can be interpreted as an indicator that the detector is oriented with the second layer vertically below the first layer and with the third layer vertically below the second layer and as an indicator of how much liquid is present as set forth in table 4.

TABLE 4

| Actual Resistance of First Layer | Actual Resistance of Second Layer | Actual Resistance of Third layer | Interpretation |
| --- | --- | --- | --- |
| Baseline | Baseline | Baseline | No Liquid Present |
| Less than baseline | Baseline | Baseline | Small amount of liquid present |
| Less than baseline | Less than baseline | Baseline | Medium amount of liquid present |
| Less than baseline | Less than baseline | Less than baseline | Large amount of liquid present. |

A second example of a liquid related occurrence which can be signified by the resistances is the spatial distribution of the liquid. For example the resistances can be interpreted as an indicator that the detector is oriented with the second layer vertically below the first layer and with the third layer vertically below the second layer and as an indicator of the distribution of the liquid as set forth in table 5.

TABLE 5

| Actual Resistance of First Layer | Actual Resistance of Second Layer | Actual Resistance of Third layer | Interpretation |
| --- | --- | --- | --- |
| Baseline | Baseline | Baseline | No Liquid Present |
| Less than baseline | Baseline | Baseline | Liquid is present predominantly at first layer |

TABLE 5-continued

| Actual Resistance of First Layer | Actual Resistance of Second Layer | Actual Resistance of Third layer | Interpretation |
|---|---|---|---|
| Less than baseline | Less than baseline | Baseline | Liquid is present predominantly at first and second layers |
| Less than baseline | Less than baseline | Less than baseline | Liquid is present at first, second and third layers. |

A third example of a liquid related occurrence which can be signified by the resistances is the severity of an incontinence event (including the limit case of no incontinence). For example the resistances can be interpreted as an indicator that the detector is oriented with the second layer vertically below the first layer and with the third layer vertically below the second layer and as an indicator of the severity of an incontinence event as set forth in table 6.

TABLE 6

| Actual Resistance of First Layer | Actual Resistance of Second Layer | Actual Resistance of Third layer | Interpretation |
|---|---|---|---|
| Baseline | Baseline | Baseline | An incontinence event has not occurred. |
| Less than baseline | Baseline | Baseline | A minor incontinence event has occurred |
| Less than baseline | Less than baseline | Baseline | A moderate incontinence event has occurred |
| Less than baseline | Less than baseline | Less than baseline | A major incontinence event has occurred |

Tables 7-9 show the three layer example of tables 4-6 generalized to N layers.

TABLE 7

| Actual Resistance of First Layer | Actual Resistance of Second Layer | ... | Actual Resistance of Nth layer | Interpretation |
|---|---|---|---|---|
| Baseline | Baseline | ... | Baseline | No Liquid Present |
| Less than baseline | Baseline | ... | Baseline | First amount of liquid present |
| Less than baseline | Less than baseline | ... | Baseline | Second amount of liquid present |
| . | . | . | . | . |
| . | . | . | . | . |
| Less than baseline | Less than baseline | ... | Less than baseline | Large amount of liquid present. |

TABLE 8

| Actual Resistance of First Layer | Actual Resistance of Second Layer | ... | Actual Resistance of Nth layer | Interpretation |
|---|---|---|---|---|
| Baseline | Baseline | ... | Baseline | No Liquid Present |
| Less than baseline | Baseline | ... | Baseline | Liquid is present predominantly at first layer |
| Less than baseline | Less than baseline | ... | Baseline | Liquid is present predominantly at first and second layers |
| . | . | . | . | . |
| . | . | . | . | . |
| Less than baseline | Less than baseline | ... | Less than baseline | Liquid is present at first through Nth layers. |

TABLE 9

| Actual Resistance of First Layer | Actual Resistance of Second Layer | ... | Actual Resistance of Nth layer | Interpretation |
|---|---|---|---|---|
| Baseline | Baseline | ... | Baseline | An incontinence event has not occurred. |
| Less than baseline | Baseline | ... | Baseline | A first severity incontinence event has occurred |
| Less than baseline | Less than baseline | ... | Baseline | A second severity incontinence event has occurred |
| . | . | . | . | . |
| . | . | . | . | . |
| Less than baseline | Less than baseline | ... | Less than baseline | An Nth severity or major incontinence event has occurred |

Figure 28:
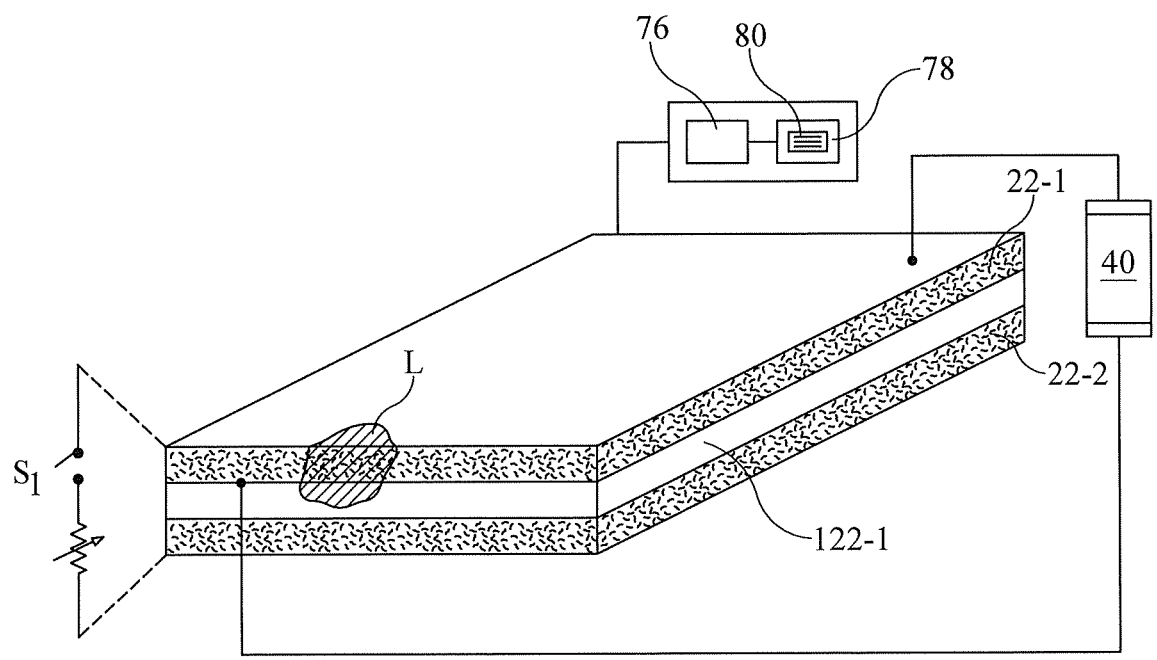
FIGS. 28-30 are views similar to FIGS. 25-27 showing embodiments which employ a single RFID tag connected across multiple layers rather than multiple RFID tags each connected across a single layer.
Figure 29:
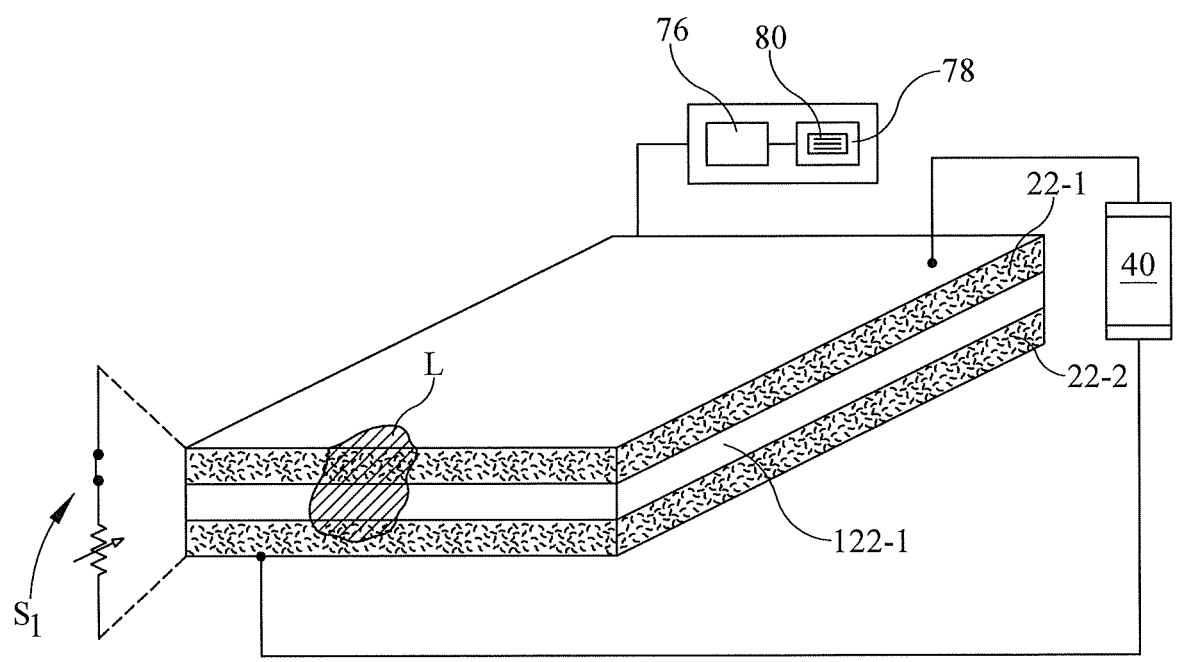
Figure 30:
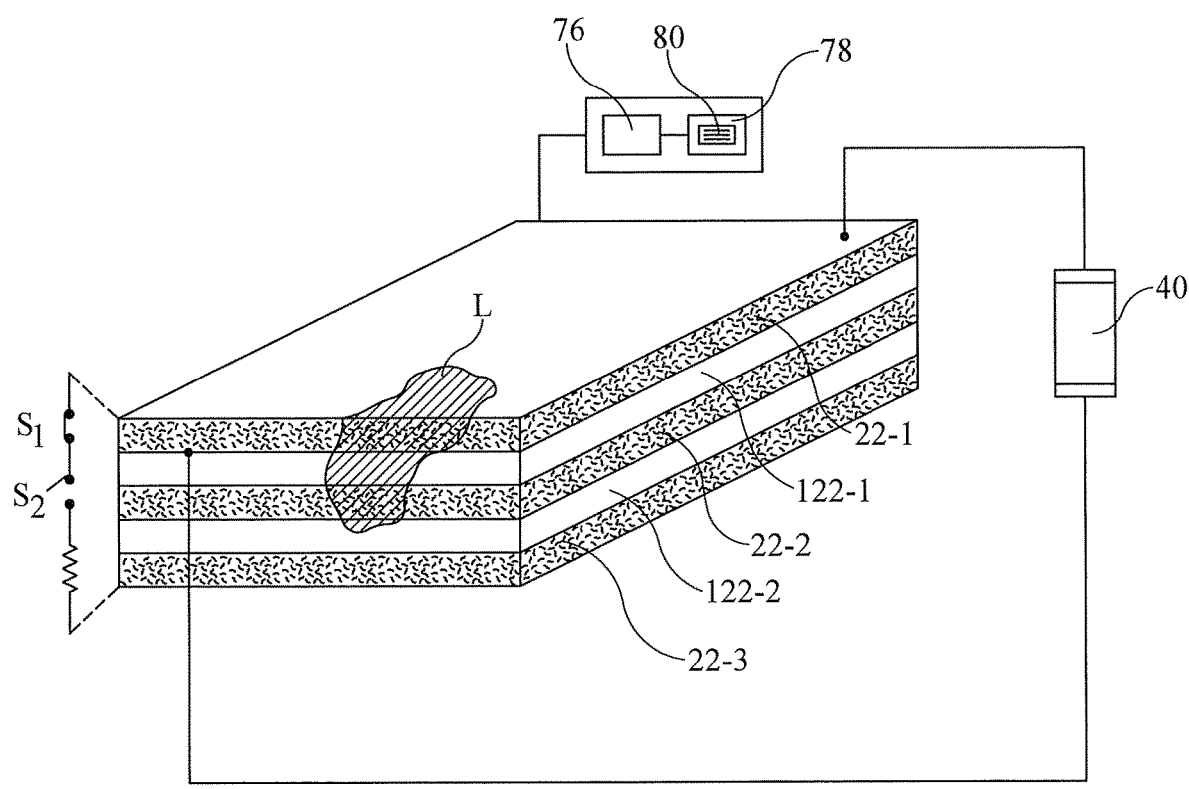

FIGS. 28-30 are views similar to FIGS. 25-27 showing embodiments which employ a single RFID tag connected across multiple layers rather than multiple RFID tags each connected across a single layer as in FIGS. 25-27.

Referring first to FIGS. 28-29, because layer 122-1 is essentially nonconductive, RFID tag 40 perceives a resistance that does not differ from the resistance it would perceive if the liquid L were not present. Not until the liquid has penetrated through layer 122-1 and into layer 22-2 does the RFID tag perceive any change in resistance. Similarly, not until the liquid has penetrated through layer 122-1 and into layer 22-2 does the processor respond with an indication that liquid is present. Thus, the arrangement of FIGS. 28-29 is less discriminating than that of FIGS. 25-26. The arrangement of FIGS. 28-29 may be of value if it is desirable to be informed of a relatively severe incontinence event but not of minor events.

Referring now to the more general example of FIG. 30, because layer 122-2 is essentially nonconductive, RFID tag 40 perceives a resistance that does not differ from the resistance it would perceive if the liquid L were not present. Not until the liquid has penetrated through layer 122-2 and into layer 22-3 does the RFID tag perceive any change in resistance. Similarly, not until the liquid has penetrated through layer 122-2 and into layer 22-3 does the processor respond with an indication that liquid is present. Thus, the arrangement of FIG. 30 is less sensitive than that of FIG. 27. The arrangement of FIGS. 28-29 may be of value if it is desirable to be informed of a relatively severe incontinence event but not of minor events.

Although this disclosure refers to specific embodiments, it will be understood by those skilled in the art that various changes in form and detail may be made without departing from the subject matter set forth in the accompanying claims.

I claim:

1. An incontinence detector for use in a multi-layer incontinence detection pad, the incontinence detector comprising:
    a layer of nonwoven material having uniformly distributed electrically resistive fiber elements that are embedded within the layer of nonwoven material so as to be dispersed uniformly throughout an entirety of a thickness, a length, and a width of the layer of nonwoven material and which impart a baseline electrical resistance to the layer, the layer also having an actual electrical resistance that varies depending upon an amount of liquid to which the layer is exposed;
    an RFID tag; and
    first and second leads which extend between the RFID tag and the material layer without contacting each other, the RFID tag being responsive to a deviation of the actual resistance when the pad is wet from the baseline resistance established when the pad is dry.

2. The incontinence detector of claim 1 further including a processor which evaluates the electrical resistance relative to the baseline resistance thereby causing the RFID tag to be responsive to the deviation of the actual resistance from the baseline resistance.

3. The incontinence detector of claim 2 wherein the evaluation of electrical resistance relative to the baseline resistance includes determining if the actual resistance of the material layer is higher than or lower than a given threshold resistance.

4. The incontinence detector of claim 1 wherein the layer of nonwoven material comprises a rectangular sheet of nonwoven material.

5. The incontinence detector of claim 1 wherein the resistive fiber elements comprise carbon fibers.

6. The incontinence detector of claim 1 wherein the layer of nonwoven material comprises a carbon fiber impregnated nonwoven material in which the carbon fibers establish the baseline resistance.

7. The incontinence detector of claim 2 wherein absorption of a liquid by the layer of nonwoven material causes the actual resistance to deviate from the baseline resistance, and the processor responds to the deviation by indicating at least one of:
    a) presence of the liquid, or
    b) identity of the liquid.

8. The incontinence detector of claim 2 wherein the actual resistance is influenced by the presence of a liquid in the layer of nonwoven material, and the detector responds by at least one of:
    a) indicating that the liquid is present, or
    b) indicating identity of the liquid.

9. The incontinence detector of claim 1 further comprising an RFID interrogator.

10. The incontinence detector of claim 6 wherein the RFID tag issues a signal consistent with the deviation of the actual resistance from the baseline resistance.

11. An incontinence detection system comprising:
    a multi-layer pad which includes carbon fiber segments that are uniformly distributed and that are embedded within a layer of nonwoven material so as to be dispersed uniformly throughout an entirety of a thickness, a length, and a width of the layer of nonwoven material and so that the pad has a dry electrical resistance when the pad is dry and a wet electrical resistance when the pad is wet with an electrically conductive liquid, the wet electrical resistance being less than the dry electrical resistance; and
    a processor and machine readable instructions which, when executed by the processor, cause the system to respond in a first way to the dry electrical resistance and to respond in a second way to the wet electrical resistance.

12. The incontinence detection system of claim 11 further comprising an RFID tag which includes the processor and a memory which holds the machine readable instructions; and
    an RFID reader for interrogating the RFID tag and receiving a return signal from the RFID tag;
    wherein the return signal includes information revealing the response of the processor to the electrical resistance of the pad.

13. The incontinence detection system of claim 12 wherein the first way of response and the second way of response distinguish between presence and absence of the electrically conductive liquid in the pad.

14. The incontinence detection system of claim 12 wherein the information permits the reader to determine an identity of a liquid to which the pad is exposed and the first way of response and the second way of response distinguish between liquids of different identities.

* * * * *